United States Patent
Lager

(10) Patent No.: US 11,891,351 B2
(45) Date of Patent: Feb. 6, 2024

(54) SYNTHESIS OF CAPSAICIN DERIVATIVES

(71) Applicant: AXICHEM AS, Kleppestø (NO)

(72) Inventor: Erik Lager, Lund (NO)

(73) Assignee: AXICHEM AS, Kleppestø (NO)

( * ) Notice: Subject to any disclaimer, the term of this patent is extended or adjusted under 35 U.S.C. 154(b) by 0 days.

(21) Appl. No.: 17/911,518

(22) PCT Filed: Mar. 19, 2021

(86) PCT No.: PCT/NO2021/050069
§ 371 (c)(1),
(2) Date: Sep. 14, 2022

(87) PCT Pub. No.: WO2021/187992
PCT Pub. Date: Sep. 23, 2021

(65) Prior Publication Data
US 2023/0060251 A1    Mar. 2, 2023

(30) Foreign Application Priority Data
Mar. 20, 2020   (NO) .................................. 20200333

(51) Int. Cl.
*C07C 233/22*   (2006.01)
*C07C 231/02*   (2006.01)

(52) U.S. Cl.
CPC .......... *C07C 233/22* (2013.01); *C07C 231/02* (2013.01)

(58) Field of Classification Search
None
See application file for complete search history.

(56) References Cited

U.S. PATENT DOCUMENTS

| | | |
|---|---|---|
| 7,446,226 B2 | 11/2008 | Helsing et al. |
| 2007/0167524 A1 | 7/2007 | Helsing et al. |
| 2017/0174618 A1 | 6/2017 | Córdova et al. |

FOREIGN PATENT DOCUMENTS

| | | |
|---|---|---|
| CN | 101717346 | 6/2010 |
| EP | 1 670 310 | 6/2006 |
| WO | 2015/144902 | 10/2015 |

OTHER PUBLICATIONS

Patil ("Lactam Synthesis via the Intramolecular Hydroamidation of Alkynes Catalyzed by Palladium Complexes" J. Org. Chem. 2006, 71, p. 3612-3614, including Supporting Information (SI) p. S-1 to S-25). (Year: 2006).*
"Denote" (https://www.merriam-webster.com/dictionary/denote, downloaded on Jul. 27, 2023): (Year: 2023).*
International Search Report (ISR) dated May 27, 2021 in International (PCT) Application No. PCT/NO2021/050069.
Norwegian Search Report dated Oct. 20, 2020 in corresponding Norwegian Patent Application No. 20200333.
Palo-Nieto, Carlos et al., "Integrated Heterogeneous Metal/Enzymatic Multiple Relay Catalysis for Eco-Friendly and Asymmetric Synthesis", ACS Catalysis, 2016, vol. 6, pp. 3932-3940.
Kaga, Harumi et al., "A General and Stereoselective Synthesis of the Capsaicinoids via the Orthoester Claisen Rearrangement", Tetrahedron, 1996, vol. 52, No. 25, pp. 8451-8470.

* cited by examiner

*Primary Examiner* — Amy C Bonaparte
(74) *Attorney, Agent, or Firm* — Wenderoth, Lind & Ponack, L.L.P.

(57) ABSTRACT

The present invention relates to the synthesis of capsaicin derivatives, specifically to the synthesis of 6-heptyne derivatives of capsaicin.

FORMULA (1)

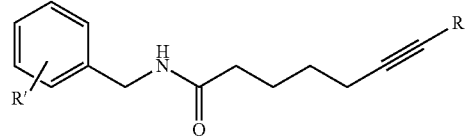

16 Claims, No Drawings

SYNTHESIS OF CAPSAICIN DERIVATIVES

FIELD OF THE INVENTION

The present invention relates to the synthesis of capsaicin derivatives, specifically to the synthesis of 6-heptyne derivatives of capsaicin.

BACKGROUND OF THE INVENTION

6-Heptyne derivatives of capsaicin, herein referred to as capsaicyns, are valuable compounds with various potential uses. Set apart from the natural compound capsaicin by their alkyne moiety replacing the alkene moiety of capsaicin, these synthetic capsaicin derivatives have found their use in various areas, including food industries, agriculture, pharmacology, and marine antifouling paint. The perhaps most widely used derivative, phenylcapsaicin N-[(4-Hydroxy-3-methoxyphenyl)methyl]-7-phenyl-6-heptynamide, has been shown to have low systemic toxicity and to be safe with regards to gene mutations and chromosomal damage (Rage Paulsen et al., *Toxicology Research and Application* 2018, 2, 1), and has been examined by the European Food Safety Authority and regarded as safe (EFSA NDA Panel et al., *EFSA Journal* 2019, 17(6), e05718).

Production of capsaicyns requires multi-step chemical synthesis. For a commercial product it is important that the synthesis is efficient and economical. Preferably the synthesis also has few synthetic steps and isolated intermediates, and is sustainable and with a low environmental impact.

Previously described syntheses of capsaicyns typically rely on coupling of the corresponding 7-substituted 6-heptynoic acid or acid chloride with vanillylamine.

In their patent EP 1670310 B1, the applicant has described the 6-step synthesis of capsaicyns, shown in Scheme 1 for phenylcapsaicin (1a).

SCHEME 1

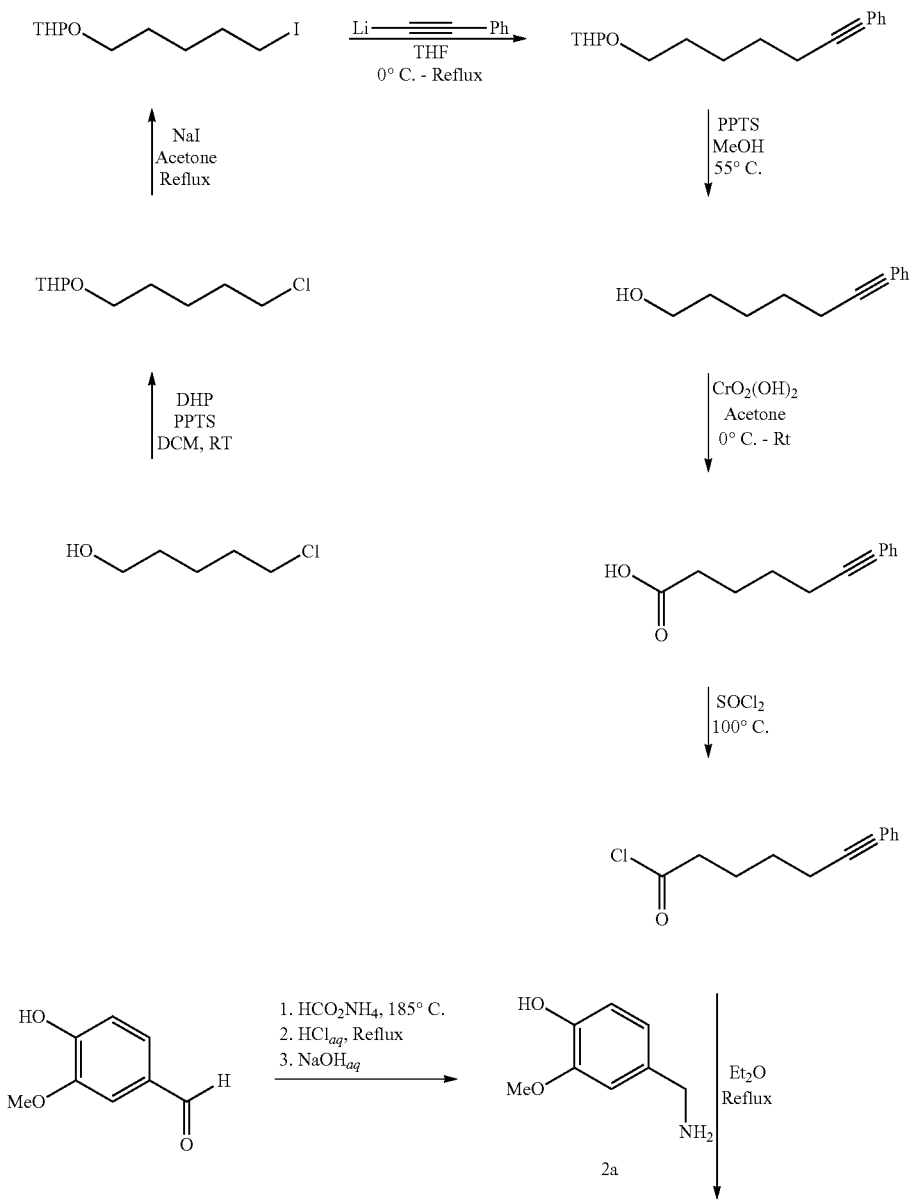

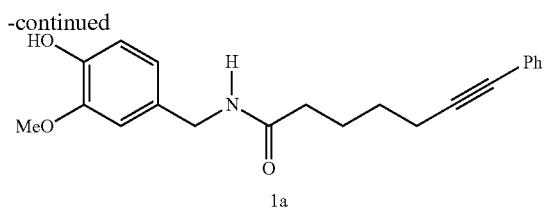

1a

The synthetic route disclosed in EP 1670310 B1 gives an overall yield of 45% starting from 5-chloro-1-pentanol. In this synthesis, as in several reported syntheses of capsaicin itself, thionyl chloride, a corrosive and reactive compound that can violently release hazardous gases upon contact with water or other reagents, is utilised in a key step.

The synthetic route provided in CN 108947863 also relies on the use of thionyl chloride in a key step.

The synthetic route in WO 2015/144902, Cordova et al., gives a yield of 78% from 6-heptynoic acid of phenylcapsaicin, but relies on palladium catalysis in the first step, with a catalyst loading of a considerable 3%. The route is shown in Scheme 2. There is a growing interest in the synthetic community to move away from the use of precious metal catalysts, as the continuous need for precious metals of low abundance not only raises economic concerns but also has significant implications for the environment (Ludwig and Schindler, *Chem* 2017, 2, 313). The high catalyst loading reported by Cordova et al. makes the synthesis very expensive to perform on a commercial scale. Further, the synthesis of 6-heptynoic acid is relatively lengthy, see Russian Chemical Bulletin 2001, 50(5), 833.

SCHEME 2

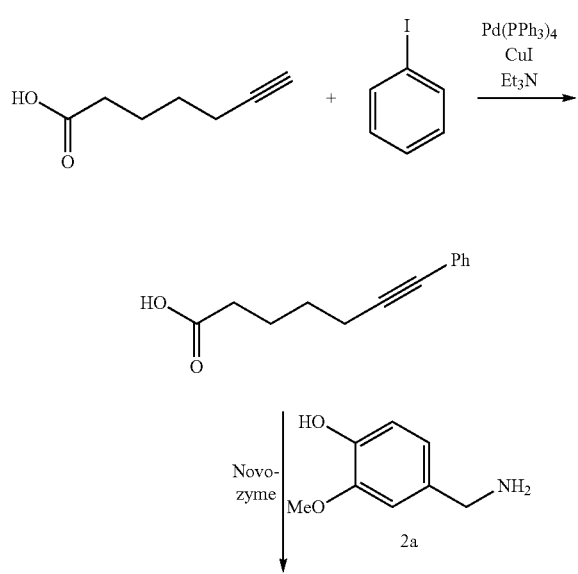

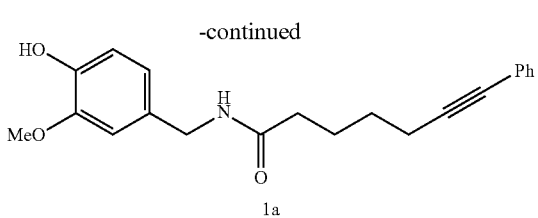

1a

For the synthesis of capsaicin itself and capsaicin derivatives without the 6-yne moiety, notable synthetic routes include thionyl chloride reliant routes via the acid chloride, similar to the route in Scheme 1 (see e.g. US 2007/0293703) and palladium catalysed (e.g. CN 107188818) and enzymatic (e.g. EO 2016/171538) coupling of the corresponding acid, as well as methods that focus on the introduction of the double bond, including Wittig reactions and Claisen ester rearrangements.

The aim of the present invention is to provide an alternative synthetic route for capsaicyns, such as a synthetic route for phenylcapsaicins, such as a synthetic route for phenylcapsaicin, such as a synthetic route that is more economic, safer, more sustainable and/or more environmentally friendly than previously described routes, and free of precious metal catalysts.

BRIEF SUMMARY OF THE INVENTION

The inventors have discovered a new synthetic route to capsaicyns. The route is shown in Scheme 3.

The new route provides the capsaicyn in three synthetic steps from readily available raw materials. With only two isolated intermediates, the route is appealing in its shortness and simplicity. The shortness of the route makes it more economic and environmentally friendly than the longer route described in EP 1670310 B1, as less solvents and fewer reagents are needed. A low number of synthetic steps also means that the output of product per time unit and reactor volume is favourable, and few isolated intermediates decreases the exposure to chemicals for operating personnel. The synthetic route is free of any metal catalysts, making it more sustainable than the route disclosed in WO 2015/144902.

SCHEME 3

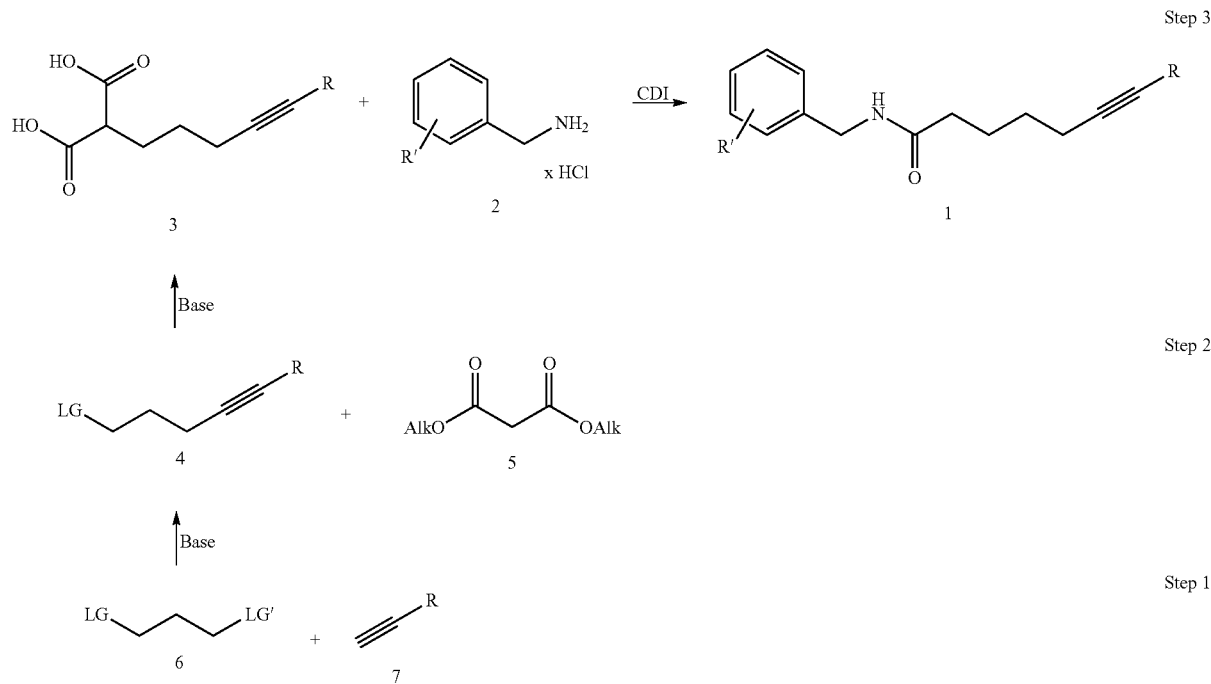

For a given synthetic route, each of R, R', Alk, LG, and LG' denotes the same substituent in all the compounds of that synthetic route.

In the presented compounds, R may be a substituent selected from the group comprising $C_1$-$C_{18}$ straight chain and branched alkyl, alkenyl, and alkynyl; trifluoromethyl; $C_3$-$C_{12}$ cycloalkyl; phenoxy; phenylthio; fluoro; chloro; bromo; iodo; phenyl; and substituted phenyl wherein the phenyl ring is substituted in any one or more positions with 1-5 identical or different substituents selected from the group comprising fluoro; chloro; bromo; iodo; cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, and CON($C_1$-$C_6$ alkyl)$_2$.

R' may represent 0-5 identical or different substituents, in any one or more positions, selected from the group comprising fluoro; chloro; bromo; iodo, hydroxy, cyano, amino, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COOH, CONH$_2$, —NHCO($C_1$-$C_6$ alkyl), COO—$C_1$-$C_6$ alkyl, CONH($C_1$-$C_6$ alkyl), and CON($C_1$-$C_6$ alkyl)$_2$.

Alk represents $C_1$-$C_6$ straight chain, branched, or cyclic alkyl. The two Alk groups may be identical.

LG and LG' represent leaving groups, that may be different from or identical to each other, selected from the list comprising, but not limited to, perfluoroalkylsulfonates such as triflates; sulfonates such as tosylates, mesylates; and fluoro; chloro; bromo; and iodo.

The present invention provides a method of preparing 6-heptyne derivatives of capsaicin of general formula 1, wherein R is a substituent selected from the group comprising $C_1$-$C_{18}$ straight chain and branched alkyl, alkenyl, and alkynyl; trifluoromethyl; $C_3$-$C_{12}$ cycloalkyl; phenoxy; phenylthio; fluoro; chloro; bromo; iodo; phenyl; and substituted phenyl, wherein said substituted phenyl ring is substituted in any one or more positions with 1-5 identical or different substituents selected from the group comprising fluoro; chloro; bromo; iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, and CON ($C_1$-$C_6$ alkyl)$_2$; and R' represents 0-5 identical or different substituents, in any one or more positions, selected from the group comprising fluoro; chloro; bromo; iodo, hydroxy, cyano, amino, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COOH, CONH$_2$, —NHCO($C_1$-$C_6$ alkyl), COO—$C_1$-$C_6$ alkyl, CONH($C_1$-$C_6$ alkyl), and CON($C_1$-$C_6$ alkyl)$_2$, the method comprising the step of coupling a compound of general formula 3 with a benzylamine of general formula 2, or any suitable salt thereof, wherein R and R' for 2 and 3 are defined as for formula 1, using 1,1'-carbonyldiimidazole (CDI).

The present invention further provides a method of preparing 6-heptyne derivatives of capsaicin of general formula 1 as described above, wherein the method further comprises, before the previously described step, the step of reacting a compound of general formula 4 with an alkyl malonate of general formula 5, wherein R for 4 is defined as for 3, to yield said compound of general formula 3; wherein Alk denotes straight chained, branched or cyclic $C_1$-$C_6$ alkyl groups; and LG denotes any leaving group well known to the person skilled in the art.

The present invention also provides a method of preparing 6-heptyne derivatives of capsaicin of general formula 1 as described above, wherein the method further comprises, before the previously described steps, the step of reacting an acetylene compound of general formula 7 and a 1,3-substituted propane compound of general formula 6, wherein LG and R for 6 and 7 are defined as for formula 4, to yield said compound of general formula 4, wherein LG and LG' are different or identical leaving groups selected from the list comprising perfluoroalkylsulfonates such as triflates; sulfonates such as tosylates, mesylates; fluoro; chloro; bromo; and iodo.

DETAILED DESCRIPTION OF THE INVENTION

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

The term "capsaicyns" as used herein refers to 6-heptyne derivatives of capsaicin, of general formula 1.

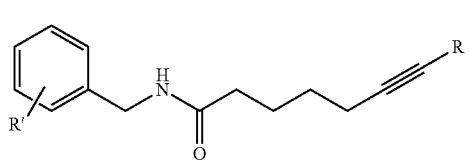

1

The skilled person knows that the terms "6-heptyne" and "hept-6-yne", both common in chemical nomenclature, can be used interchangeably and has the same meaning. The choice to use the term "6-heptyne", and related nomenclature such as "6-heptynoic", etc., herein is purely for the purpose of readability.

The reader should note that the nomenclature used for capsaicin derivatives in the art is not consistent, and that while the term capsaicyns is used, for ease of reading, when reference is made to the general group of compounds, the well-established common name "phenylcapsaicin" will be used when referring to N-[(4-Hydroxy-3-methoxyphenyl)methyl]-7-phenyl-6-heptynamide, and "phenylcapsaicins" will be used to refer to derivatives thereof.

The term "derivative" as used herein refers to a molecule that differs in chemical structure from a parent compound. Examples of derivatives include, without limitation: homologues, which differ incrementally from the chemical structure of the parent, such as a difference in the length of an aliphatic chain; molecular fragments; structures that differ by one or more functional groups from the parent compound, such as can be made by transforming one or more functional groups of a parent; a change in ionization state of a parent, such as ionising an acid to its conjugate base; isomers, including positional, geometric and stereoisomers; and combinations thereof.

As used herein, the term "$C_1$-$C_6$ alkyl" refers to the straight and branched aliphatic radicals of 1 to 6 carbon atoms, such as methyl, ethyl, propyl, isopropyl, butyl, tert-butyl, sec-butyl, isobutyl, pentyl, hexyl, and the like. The term "$C_1$-$C_6$ straight chain and branched alkoxy" refers to methoxy, ethoxy, propoxy, isopropoxy, butoxy, sec-butoxy, isobutoxy, and tert-butoxy, and the like.

The term "solvent" as used herein refers to a liquid substance in which a compound is soluble or partially soluble enough at a given concentration to dissolve or partially dissolve the compound. The term refers both to solvent blends (i.e., solvents consisting of a plurality of constituents) and to pure compounds (i.e., solvents consisting of a single constituent) unless the context indicates otherwise.

The term "anhydrous solvent" as used herein refers to solvents containing less than 0.5% by weight water, preferably maintained and handled under nitrogen or argon gas during a reaction.

The term "anhydrous conditions" as used herein refers to the avoidance in the reaction mixture of any substantial amount of moisture, such as the reaction mixture containing less than 0.5% by weight water, but is not intended to mean the total absence of any moisture.

The term "base" as used herein means a compound capable of accepting a proton.

The term "simultaneously" as used herein refers to any two or more processes that are occurring at the same time or roughly at the same time, and is not to be understood strictly. It is not intended that the processes need to begin nor end together.

The term "quench the reaction mixture" as used herein means to inactivate a reagent, and/or to stop the reaction, and/or to initiate work-up of the reaction mixture.

The phenyl rings are numbered cyclically from 1 to 6 starting at the ipso carbon (1), regardless of the priority of any substituents.

It is clear to the person skilled in the art that not only the compounds disclosed herein, but also a wide range of derivatives, analogues, and/or salts, in various stereoisomeric forms, can also be synthesised in accordance with the present invention, using the disclosed method of preparing 6-heptyne derivatives of capsaicin.

It is further clear to the person skilled in the art that the product obtained in any of the reactions disclosed herein may be in the form of a solvate, such as a hydrate, and/or may contain impurities. The skilled person is knowledgeable about a range of different techniques for removing any solvent rests. The skilled person is knowledgeable about a range of different purification techniques.

In some embodiments, the invention provides a synthetic route to capsaicyns of general structure 1, wherein R is a substituent selected from the group comprising hydrogen, $C_1$-$C_{18}$ straight chain and branched alkyl, alkenyl, and alkynyl; trifluoromethyl; $C_3$-$C_{12}$ cycloalkyl; phenoxy; phenylthio; fluoro; chloro; bromo; iodo; phenyl; and substituted phenyl;

wherein said substituted phenyl is substituted in any one or more positions with 1-5 identical or different substituents selected from the group comprising fluoro; chloro; bromo; iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, alkenyl, and alkynyl $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, and CON($C_1$-$C_6$ alkyl)$_2$; and R' represents 0-5 identical or different substituents, in any one or more positions, selected from the group comprising fluoro; chloro; bromo; iodo, hydroxy, cyano, amino, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, alkenyl, and alkynyl, $C_1$-$C_6$ fluoroalkyl, chloroalkyl, bromoalkyl, and iodoalkyl, COOH, $CONH_2$, —NHCO($C_1$-$C_6$ alkyl), COO—$C_1$-$C_6$ alkyl, CONH($C_1$-$C_6$ alkyl), and CON($C_1$-$C_6$ alkyl)$_2$.

In some embodiments, the invention provides a synthetic route to capsaicyns of general structure 1, wherein R is a substituent selected from the group consisting of hydrogen, $C_1$-$C_{18}$ straight chain and branched alkyl, alkenyl, and alkynyl; trifluoromethyl; $C_3$-$C_{12}$ cycloalkyl; phenoxy; phenylthio; fluoro; chloro; bromo; iodo; phenyl; and substituted phenyl;

wherein said substituted phenyl is substituted in any one or more positions with 1-5 identical or different substituents selected from the group consisting of fluoro; chloro; bromo; iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, alkenyl, and alkynyl $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, and CON ($C_1$-$C_6$ alkyl)$_2$; and R' represents 0-5 identical or different substituents, in any one or more positions, selected from the group consisting of fluoro; chloro; bromo; iodo, hydroxy, cyano, amino, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, alkenyl, and alkynyl, $C_1$-$C_6$ fluoroalkyl, chloroalkyl, bromoalkyl, and iodoalkyl, COOH, $CONH_2$, —NHCO($C_1$-$C_6$ alkyl), COO—$C_1$-$C_6$ alkyl, CONH($C_1$-$C_6$ alkyl), and CON($C_1$-$C_6$ alkyl)$_2$.

Said substituted phenyl may be substituted in any one or more positions with 1-5 identical or different substituents selected from the group comprising or consisting of fluoro; chloro; bromo; iodo; cyano; nitro; trifluoromethyl; $C_1$-$C_6$ straight chain and branched alkoxy; $C_1$-$C_6$ sulfoxy; —S—$C_1$-$C_6$ alkyl; $C_1$-$C_{12}$ straight chain and branched alkyl, alkenyl, and alkynyl; $C_1$-$C_6$ fluoroalkyl, chloroalkyl, bromoalkyl, and iodoalkyl; COO—$C_1$-$C_6$ alkyl; and CON($C_1$-$C_6$ alkyl)$_2$. Such variants are denoted a1.

Said substituted phenyl may be substituted in any one or more positions with 1-5 identical or different substituents selected from the group comprising or consisting of fluoro; chloro; bromo; iodo; cyano; nitro; trifluoromethyl; $C_1$-$C_6$ straight chain and branched alkoxy; $C_1$-$C_6$ sulfoxy; —S—$C_1$-$C_6$ alkyl; $C_1$-$C_{12}$ straight chain and branched alkyl, alkenyl, and alkynyl; and $C_1$-$C_6$ fluoroalkyl, chloroalkyl, bromoalkyl, and iodoalkyl. Such variants are denoted a2.

Said substituted phenyl may be substituted in any one or more positions with 1-5 identical or different substituents selected from the group comprising or consisting of fluoro; chloro; bromo; iodo; cyano; nitro; and trifluoromethyl. Such variants are denoted a3.

Said substituted phenyl may be substituted in any one or more positions with 1-5 identical or different substituents selected from the group comprising or consisting of fluoro; chloro; bromo; iodo; $C_1$-$C_{12}$ straight chain and branched alkyl, alkenyl, and alkynyl; and $C_1$-$C_6$ straight chain and branched alkoxy. Such variants are denoted a4.

Said substituted phenyl may be substituted in any one or more positions with 1-5 identical or different substituents selected from the group comprising or consisting of fluoro; chloro; bromo; iodo; $C_1$-$C_{10}$ straight chain and branched alkyl, alkenyl, and alkynyl; and $C_1$-$C_6$ straight chain and branched alkoxy. Such variants are denoted a5.

Said substituted phenyl ring may be substituted in any one or more positions with 1-5 identical or different substituents selected from the group comprising or consisting of nitro; $C_1$-$C_6$ straight chain and branched alkyl, alkenyl, and alkynyl; and $C_1$-$C_4$ straight chain and branched alkoxy. Such variants are denoted a6.

Said substituted phenyl may be substituted in any one or more positions with 1-5 identical or different substituents selected from the group comprising or consisting of $C_1$-$C_6$ straight chain and branched alkyl, alkenyl, and alkynyl; and $C_1$-$C_6$ fluoroalkyl, chloroalkyl, bromoalkyl, and iodoalkyl. Such variants are denoted a7.

Said substituted phenyl may have one substituent, such as in 2-position, such as in 3-position, such as in 4-position. Said phenyl ring may have two substituents, such as in positions 2 and 6, such as in positions 2 and 5, such as in positions 2 and 3, such as in positions 3 and 5, such as in positions 2 and 4, such as in positions 3 and 4. Said phenyl ring may have three substituents, such as in positions 2, 3, and 6, such as in positions 2, 4, and 6, such as in positions 2, 3, and 4, such as in positions 2, 3, and 5, such as in positions 3, 4, and 5. Said phenyl ring may have four substituents, such as in positions 2, 3, 4, and 6, such as in positions 2, 3, 4, and 5, such as in positions 2, 3, 5, and 6. Said phenyl ring may have five substituents.

In some variants, two of said substituents on the substituted phenyl are identical to each other. In some variants, three of the substituents are identical to each other. In some variants, four of the substituents are identical to each other. In some variants, five of the substituents are identical to each other. In other variants, all of said substituents are different from each other.

R may be selected from the group comprising or consisting of hydrogen, $C_1$-$C_{18}$ straight chain and branched alkyl, alkenyl, and alkynyl; trifluoromethyl; $C_3$-$C_{12}$ cycloalkyl; phenoxy; phenylthio; fluoro; chloro; bromo; iodo; phenyl; and substituted phenyl as defined above. Such variants are denoted b1.

R may be selected from the group comprising or consisting of $C_1$-$C_{18}$ straight chain and branched alkyl, alkenyl, and alkynyl; phenyl; and substituted phenyl as defined above. Such variants are denoted b2.

R may be selected from the group comprising or consisting of hydrogen, $C_1$-$C_{10}$ straight chain and branched alkyl, alkenyl, and alkynyl; trifluoromethyl; $C_3$-$C_8$ cycloalkyl; phenoxy; phenylthio; fluoro; chloro; bromo; iodo; phenyl; and substituted phenyl as defined above. Such variants are denoted b3.

R may be selected from the group comprising or consisting of $C_1$-$C_6$ straight chain and branched alkyl, alkenyl, and alkynyl; trifluoromethyl; $C_3$-$C_6$ cycloalkyl; phenoxy; phenylthio; fluoro; chloro; bromo; iodo; phenyl; and substituted phenyl as defined above. Such variants are denoted b4.

R may be selected from the group comprising or consisting of $C_1$-$C_{18}$ straight chain and branched alkyl, alkenyl, and alkynyl; trifluoromethyl; $C_3$-$C_{12}$ cycloalkyl; fluoro; chloro; bromo; iodo; phenyl; and substituted phenyl as defined above. Such variants are denoted b5.

R may be selected from the group comprising or consisting of $C_1$-$C_{10}$ straight chain and branched alkyl, alkenyl, and alkynyl; $C_3$-$C_8$ cycloalkyl; and phenyl. Such variants are denoted b6.

Preferably, R is an unsubstituted phenyl ring. Such variants are denoted b7.

All variants described as comprising a substituted phenyl may comprise any of the variants a1-a7 of substituted phenyl rings, resulting in the following R groups:

a1+b1, a1+b2, a1+b3, a1+b4, a1+b5, a2+b1, a2+b2, a2+b3, a2+b4, a2+b5, a3+b1, a3+b2, a3+b3, a3+b4, a3+b5, a4+b1, a4+b2, a4+b3, a4+b4, a4+b5, a5+b1, a5+b2, a5+b3, a5+b4, a5+b5, a6+b1, a6+b2, a6+b3, a6+b4, a6+b5, a7+b1, a7+b2, a7+b3, a7+b4, a7+b5, b6, b7.

The letter-number combinations refer to the variants defined above, so that e.g. a1+b1 means that R may be selected from the group comprising or consisting of hydrogen, $C_1$-$C_{18}$ straight chain and branched alkyl, alkenyl, and alkynyl; trifluoromethyl; $C_3$-$C_{12}$ cycloalkyl; phenoxy; phenylthio; fluoro; chloro; bromo; iodo; phenyl; and substituted phenyl (b1), wherein said substituted phenyl may be substituted in any one or more positions with 1-5 identical or different substituents selected from the group comprising or consisting of fluoro; chloro; bromo; iodo; cyano; nitro; trifluoromethyl; $C_1$-$C_6$ straight chain and branched alkoxy; $C_1$-$C_6$ sulfoxy; —S—$C_1$-$C_6$ alkyl; $C_1$-$C_{12}$ straight chain and branched alkyl, alkenyl, and alkynyl; $C_1$-$C_6$ fluoroalkyl, chloroalkyl, bromoalkyl, and iodoalkyl; COO—$C_1$-$C_6$ alkyl; and CON($C_1$-$C_6$ alkyl)$_2$ (a1); and a7+b5 means that R may be selected from the group comprising or consisting of $C_1$-$C_{18}$ straight chain and branched alkyl, alkenyl, and alkynyl; trifluoromethyl; $C_3$-$C_{12}$ cycloalkyl; fluoro; chloro; bromo; iodo; phenyl; and substituted phenyl, wherein said substituted phenyl may be substituted in any one or more positions with 1-5 identical or different substituents selected from the group comprising or consisting of $C_1$-$C_6$ straight chain and branched alkyl, alkenyl, and alkynyl; and $C_1$-$C_6$ fluoroalkyl, chloroalkyl, bromoalkyl, and iodoalkyl (a7), and so on.

R' may represent 0-5 identical or different substituents, in any one or more positions, selected from the group comprising or consisting of: fluoro; chloro; bromo; iodo; hydroxy; cyano; amino; nitro; trifluoromethyl; $C_1$-$C_6$ straight chain and branched alkoxy; $C_1$-$C_6$ sulfoxy; —S—$C_1$-$C_6$ alkyl; $C_1$-$C_{12}$ straight chain and branched alkyl, alkenyl, and alkynyl; $C_1$-$C_6$ fluoroalkyl, chloroalkyl, bromoalkyl, and iodoalkyl; COOH; CONH$_2$; —NHCO($C_1$-$C_6$ alkyl); COO—$C_1$-$C_6$ alkyl; CONH($C_1$-$C_6$ alkyl); and CON($C_1$-$C_6$ alkyl)$_2$. Such variants are denoted c1.

R' may represent 0-5 identical or different substituents, in any one or more positions, selected from the group comprising or consisting of fluoro, chloro, bromo, iodo, hydroxy, cyano, amino nitro, trifluoromethyl, COOH—NHCO($C_1$-$C_6$ alkyl) and CONH$_2$. Such variants are denoted c2.

R' may represent 0-5 identical or different substituents, in any one or more positions, selected from the group comprising or consisting of hydroxy, methoxy, fluoro, chloro, bromo, and iodo. Such variants are denoted c3.

Preferably, R' represents 0-5 identical or different substituents, in any one or more positions, selected from the group comprising or consisting of hydroxy, methoxy, iodo, bromo, and chloro. Such variants are denoted c4.

R' may represent zero substituents, meaning that the phenyl ring drawn with R' on as a substituent is in fact unsubstituted. R' may represent one substituent, such as in 2-position, such as in 3-position, such as in 4-position. R' may represent two substituents, such as in positions 2 and 6, such as in positions 2 and 5, such as in positions 2 and 3, such as in positions 3 and 5, such as in positions 2 and 4, such as in positions 3 and 4. R' may represent three substituents, such as in positions 2, 3, and 6, such as in positions 2, 4, and 6, such as in positions 2, 3, and 4, such as in positions 2, 3, and 5, such as in positions 3, 4, and 5. R' may represent four substituents, such as in positions 2, 3, 4, and 6, such as in positions 2, 3, 4, and 5, such as in positions 2, 3, 5, and 6. R' may represent five substituents.

Preferably, R' represents two substituents, in positions 3 and 4.

In some variants, two of said substituents are identical to each other. In some variants, three of the substituents are identical to each other. In some variants, four of the substituents are identical to each other. In some variants, five of the substituents are identical to each other. In other variants, all of said substituents are different from each other.

In preferred variants, R' represents the two substituents 3-methoxy and 4-hydroxy.

It is to be understood that each selection of possible R group, R' group, and substituents on the phenyl ring disclosed herein is to be interpreted as being disclosed for use in any combination with one or more of each and every other election of possible R group, R' group and substituents on the phenyl ring disclosed herein.

Thus, in some embodiments, the invention provides a synthetic route to capsaicyns of general structure 1 and R and R' as listed below:

a1+b1+c1, a1+b2+c1, a1+b3+c1, a1+b4+c1, a1+b5+c1, a2+b1+c1, a2+b2+c1, a2+b3+c1, a2+b4+c1, a2+b5+c1, a3+b1+c1, a3+b2+c1, a3+b3+c1, a3+b4+c1, a3+b5+c1, a4+b1+c1, a4+b2+c1, a4+b3+c1, a4+b4+c1, a4+b5+c1, a5+b1+c1, a5+b2+c1, a5+b3+c1, a5+b4+c1, a5+b5+c1, a6+b1+c1, a6+b2+c1, a6+b3+c1, a6+b4+c1, a6+b5+c1, a7+b1+c1, a7+b2+c1, a7+b3+c1, a7+b4+c1, a7+b5+c1, b6+c1, b7+c1, a1+b1+c2, a1+b2+c2, a1+b3+c2, a1+b4+c2, a1+b5+c2, a2+b1+c2, a2+b2+c2, a2+b3+c2, a2+b4+c2, a2+b5+c2, a3+b1+c2, a3+b2+c2, a3+b3+c2, a3+b4+c2, a3+b5+c2, a4+b1+c2, a4+b2+c2, a4+b3+c2, a4+b4+c2, a4+b5+c2, a5+b1+c2, a5+b2+c2, a5+b3+c2, a5+b4+c2, a5+b5+c2, a6+b1+c2, a6+b2+c2, a6+b3+c2, a6+b4+c2, a6+b5+c2, a7+b1+c2, a7+b2+c2, a7+b3+c2, a7+b4+c2, a7+b5+c2, b6+c2, b7+c2, a1+b1+c3, a1+b2+c3, a1+b3+c3, a1+b4+c3, a1+b5+c3, a2+b1+c3, a2+b2+c3, a2+b3+c3, a2+b4+c3, a2+b5+c3, a3+b1+c3, a3+b2+c3, a3+b3+c3, a3+b4+c3, a3+b5+c3, a4+b1+c3, a4+b2+c3, a4+b3+c3, a4+b4+c3, a4+b5+c3, a5+b1+c3, a5+b2+c3, a5+b3+c3, a5+b4+c3, a5+b5+c3, a6+b1+c3, a6+b2+c3, a6+b3+c3, a6+b4+c3, a6+b5+c3, a7+b1+c3, a7+b2+c3, a7+b3+c3, a7+b4+c3, a7+b5+c3, b6+c3, b7+c3, a1+b1+c4, a1+b2+c4, a1+b3+c4, a1+b4+c4, a1+b5+c4, a2+b1+c4, a2+b2+c4, a2+b3+c4, a2+b4+c4, a2+b5+c4, a3+b1+c4, a3+b2+c4, a3+b3+c4, a3+b4+c4, a3+b5+c4, a4+b1+c4, a4+b2+c4, a4+b3+c4, a4+b4+c4, a4+b5+c4, a5+b1+c4, a5+b2+c4, a5+b3+c4, a5+b4+c4, a5+b5+c4, a6+b1+c4, a6+b2+c4, a6+b3+c4, a6+b4+c4, a6+b5+c4, a7+b1+c4, a7+b2+c4, a7+b3+c4, a7+b4+c4, a7+b5+c4, b6+c4, b7+c4.

The letter-number combinations refer to the variants defined above, so that e.g. a1+b1+c1 denotes a compound wherein R is selected from the group comprising or consisting of hydrogen, $C_1$-$C_{18}$ straight chain and branched alkyl, alkenyl, and alkynyl; trifluoromethyl; $C_3$-$C_{12}$ cycloalkyl; phenoxy; phenylthio; fluoro; chloro; bromo; iodo; phenyl; and substituted phenyl (b1), wherein said substituted phenyl may be substituted in any one or more positions with 1-5 identical or different substituents selected from the group comprising or consisting of fluoro; chloro; bromo; iodo; cyano; nitro; trifluoromethyl; $C_1$-$C_6$ straight chain and branched alkoxy; $C_1$-$C_6$ sulfoxy; —S—$C_1$-$C_6$ alkyl; $C_1$-$C_{12}$ straight chain and branched alkyl, alkenyl, and alkynyl; $C_1$-$C_6$ fluoroalkyl, chloroalkyl, bromoalkyl, and iodoalkyl;

COO—$C_1$-$C_6$ alkyl; and CON($C_1$-$C_6$ alkyl)$_2$ (a1), and R' represents 0-5 identical or different substituents, in any one or more positions, selected from the group comprising or consisting of fluoro; chloro; bromo; iodo; hydroxy; cyano; amino; nitro; trifluoromethyl; $C_1$-$C_6$ straight chain and branched alkoxy; $C_1$-$C_6$ sulfoxy; —S—$C_1$-$C_6$ alkyl; $C_1$-$C_{12}$ straight chain and branched alkyl, alkenyl, and alkynyl; $C_1$-$C_6$ fluoroalkyl, chloroalkyl, bromoalkyl, and iodoalkyl; COOH; CONH$_2$; —NHCO($C_1$-$C_6$ alkyl); COO—$C_1$-$C_6$ alkyl; CONH($C_1$-$C_6$ alkyl); and CON($C_1$-$C_6$ alkyl)$_2$ (c1), and so on.

In preferred embodiments, the invention provides a synthetic route to capsaicyns of general structure 1 and R and R' as listed below:

a1+b1+c1, a1+b2+c1, a1+b3+c1, a1+b4+c1, a1+b5+c1, a2+b1+c1, a2+b2+c1, a2+b3+c1, a2+b4+c1, a2+b5+c1, a3+b1+c1, a3+b2+c1, a3+b3+c1, a3+b4+c1, a3+b5+c1, a4+b1+c1, a4+b2+c1, a4+b3+c1, a4+b4+c1, a4+b5+c1, a5+b1+c1, a5+b2+c1, a5+b3+c1, a5+b4+c1, a5+b5+c1, a6+b1+c1, a6+b2+c1, a6+b3+c1, a6+b4+c1, a6+b5+c1, a7+b1+c1, a7+b2+c1, a7+b3+c1, a7+b4+c1, a7+b5+c1, b6+c1, b7+c1, a1+b1+c2, a1+b2+c2, a1+b3+c2, a1+b4+c2, a1+b5+c2, a2+b1+c2, a2+b2+c2, a2+b3+c2, a2+b4+c2, a2+b5+c2, a3+b1+c2, a3+b2+c2, a3+b3+c2, a3+b4+c2, a3+b5+c2, a4+b1+c2, a4+b2+c2, a4+b3+c2, a4+b4+c2, a4+b5+c2, a5+b1+c2, a5+b2+c2, a5+b3+c2, a5+b4+c2, a5+b5+c2, a6+b1+c2, a6+b2+c2, a6+b3+c2, a6+b4+c2, a6+b5+c2, a7+b1+c2, a7+b2+c2, a7+b3+c2, a7+b4+c2, a7+b5+c2, b6+c2, b7+c2, a1+b1+c3, a1+b2+c3, a1+b3+c3, a1+b4+c3, a1+b5+c3, a2+b1+c3, a2+b2+c3, a2+b3+c3, a2+b4+c3, a2+b5+c3, a3+b1+c3, a3+b2+c3, a3+b3+c3, a3+b4+c3, a3+b5+c3, a4+b1+c3, a4+b2+c3, a4+b3+c3, a4+b4+c3, a4+b5+c3, a5+b1+c3, a5+b2+c3, a5+b3+c3, a5+b4+c3, a5+b5+c3, a6+b1+c3, a6+b2+c3, a6+b3+c3, a6+b4+c3, a6+b5+c3, a7+b1+c3, a7+b2+c3, a7+b3+c3, a7+b4+c3, a7+b5+c3, b6+c3, b7+c3, a1+b1+c4, a1+b2+c4, a1+b3+c4, a1+b4+c4, a1+b5+c4, a2+b1+c4, a2+b2+c4, a2+b3+c4, a2+b4+c4, a2+b5+c4, a3+b1+c4, a3+b2+c4, a3+b3+c4, a3+b4+c4, a3+b5+c4, a4+b1+c4, a4+b2+c4, a4+b3+c4, a4+b4+c4, a4+b5+c4, a5+b1+c4, a5+b2+c4, a5+b3+c4, a5+b4+c4, a5+b5+c4, a6+b1+c4, a6+b2+c4, a6+b3+c4, a6+b4+c4, a6+b5+c4, a7+b1+c4, a7+b2+c4, a7+b3+c4, a7+b4+c4, a7+b5+c4, b6+c4, b7+c4, wherein R' represents two substituents, in positions 3 and 4, preferably R' represents the two substituents 3-methoxy and 4-hydroxy.

In preferred embodiments, the invention provides a synthetic route to capsaicyns of general structure 1 and R and R' as listed below:

a1+b1+c1, a1+b2+c1, a1+b3+c1, a1+b4+c1, a1+b5+c1, a2+b1+c1, a2+b2+c1, a2+b3+c1, a2+b4+c1, a2+b5+c1, a3+b1+c1, a3+b2+c1, a3+b3+c1, a3+b4+c1, a3+b5+c1, a4+b1+c1, a4+b2+c1, a4+b3+c1, a4+b4+c1, a4+b5+c1, a5+b1+c1, a5+b2+c1, a5+b3+c1, a5+b4+c1, a5+b5+c1, a6+b1+c1, a6+b2+c1, a6+b3+c1, a6+b4+c1, a6+b5+c1, a7+b1+c1, a7+b2+c1, a7+b3+c1, a7+b4+c1, a7+b5+c1, b6+c1, b7+c1, a1+b1+c2, a1+b2+c2, a1+b3+c2, a1+b4+c2, a1+b5+c2, a2+b1+c2, a2+b2+c2, a2+b3+c2, a2+b4+c2, a2+b5+c2, a3+b1+c2, a3+b2+c2, a3+b3+c2, a3+b4+c2, a3+b5+c2, a4+b1+c2, a4+b2+c2, a4+b3+c2, a4+b4+c2, a4+b5+c2, a5+b1+c2, a5+b2+c2, a5+b3+c2, a5+b4+c2, a5+b5+c2, a6+b1+c2, a6+b2+c2, a6+b3+c2, a6+b4+c2, a6+b5+c2, a7+b1+c2, a7+b2+c2, a7+b3+c2, a7+b4+c2, a7+b5+c2, b6+c2, b7+c2, a1+b1+c3, a1+b2+c3, a1+b3+c3, a1+b4+c3, a1+b5+c3, a2+b1+c3, a2+b2+c3, a2+b3+c3, a2+b4+c3, a2+b5+c3, a3+b1+c3, a3+b2+c3, a3+b3+c3, a3+b4+c3, a3+b5+c3, a4+b1+c3, a4+b2+c3, a4+b3+c3, a4+b4+c3, a4+b5+c3, a5+b1+c3, a5+b2+c3, a5+b3+c3, a5+b4+c3, a5+b5+c3, a6+b1+c3, a6+b2+c3, a6+b3+c3, a6+b4+c3, a6+b5+c3, a7+b1+c3, a7+b2+c3, a7+b3+c3, a7+b4+c3, a7+b5+c3, b6+c3, b7+c3, a1+b1+c4, a1+b2+c4, a1+b3+c4, a1+b4+c4, a1+b5+c4, a2+b1+c4, a2+b2+c4, a2+b3+c4, a2+b4+c4, a2+b5+c4, a3+b1+c4, a3+b2+c4, a3+b3+c4, a3+b4+c4, a3+b5+c4, a4+b1+c4, a4+b2+c4, a4+b3+c4, a4+b4+c4, a4+b5+c4, a5+b1+c4, a5+b2+c4, a5+b3+c4, a5+b4+c4, a5+b5+c4, a6+b1+c4, a6+b2+c4, a6+b3+c4, a6+b4+c4, a6+b5+c4, a7+b1+c4, a7+b2+c4, a7+b3+c4, a7+b4+c4, a7+b5+c4, b6+c4, b7+c4, each of the letter-number combinations referring to the variants consisting of the substituents as listed above, wherein R' represents two substituents, in positions 3 and 4, preferably R' represents the two substituents 3-methoxy and 4-hydroxy.

In other preferred embodiments, the invention provides a synthetic route to phenylcapsaicins of general structure 1 and R and R' as listed below:

b7+c1, b7+c2, b7+c3, b7+c4, preferably wherein R' represents two substituents, in positions 3 and 4, more preferably R' represents the two substituents 3-methoxy and 4-hydroxy.

In further preferred embodiments, the invention provides a synthetic route to phenylcapsaicins of general structure 1 and R and R' as listed below:

b7+c1, b7+c2, b7+c3, b7+c4, each of the letter-number combinations referring to the variants consisting of the substituents as listed above, preferably wherein R' represents two substituents, in positions 3 and 4, more preferably R' represents the two substituents 3-methoxy and 4-hydroxy.

Non-limiting examples of capsaicin derivatives that can be synthesised according to the invention include N-[(4-Hydroxy-3-methoxyphenyl)methyl]-7-phenyl-6-heptynamide (phenylcapsaicin, 1a)

N-Benzyl-7-phenyl-6-heptynamide

N-[(4-Hydroxy-3-methoxyphenyl)methyl]-7-cyclohexyl-6-heptynamide (1c)

N-[(4-Hydroxy-3-methoxyphenyl)methyl]-10-ethyl-6-dodecynamide

N-[(4-Hydroxy-3-methoxyphenyl)methyl]-8,8,8-trifluoro-6-octynamide

N-(3-Hexylphenyl)methyl-7-phenyl-6-heptynamide N-[(4-Hydroxy-3-methoxyphenyl)methyl]-7-(3,5-diethoxyphenyl)-6-heptynamide N-[(4-Hydroxy-3-methoxyphenyl)methyl]-6-octynamide N-[(4-Hydroxy-3-methoxyphenyl)methyl]-6-nonynamide N-[(4-Hydroxy-3-methoxyphenyl)methyl]-8-methyl-6-nonynamide N-[(4-Hydroxy-3-methoxyphenyl)methyl]-8,8-dimethyl-6-nonynamide (1b)

N-(3,4-Dibromophenyl)methyl-7-phenyl-6-heptynamide

N-[(3-Ethyl-2-isopropyl-6-methylphenyl)methyl]-7-(2,6-xylyl)-6-heptynamide

N-(3,5-Diethoxyphenyl)methyl-7-(p-fluorophenyl)-6-heptynamide

N-[(4-Hydroxy-3-methoxyphenyl)methyl]-7-bromo-6-heptynamide

N-[(4-Hydroxy-3-methoxyphenyl)methyl]-7-cyclopentyl-6-heptynamide

In some embodiments, the invention provides a synthetic route to phenyl-substituted 6-yne derivatives of capsaicin, often referred to as phenylcapsaicins, wherein R is phenyl or substituted phenyl and R' represents the two substituents 3-methoxy and 4-hydroxy.

In one specific embodiment, the invention provides a synthetic route to phenylcapsaicin, wherein R is phenyl and R' represents the two substituents 3-methoxy and 4-hydroxy.

Step 3

In all embodiments, capsaicin derivative 1 is synthesised from precursor 3 and a benzylamine 2. This step is referred to as Step 3. Treatment with 1,1'-carbonyldiimidazole (CDI) gives product 1 under mild conditions. The reaction is performed using the method first presented by Lafrance et al. [Lafrance et al., *Org. Lett.* 2011, 13(9), 2322], and is believed to proceed via a carbonyl imidazole intermediate. Step 3 is shown in Scheme 4.

During the development of the synthetic route, the inventors discovered that decarboxylation of diacid 3 followed by transformation to the corresponding acid chloride for coupling with 2, was surprisingly challenging. This possible decarboxylation/coupling route, more similar to the previously reported thionyl chloride reliant routes, had the disadvantage that the decarboxylation required high temperatures and was best performed neat, thus limiting the reaction scope. The present invention solves this problem by the elegant CDI coupling utilising diacid 3 directly and circumventing the need for a separate decarboxylation step.

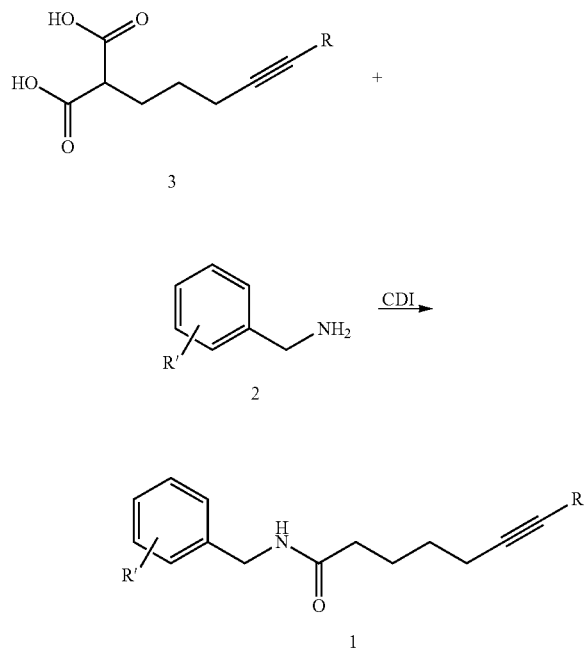

The reactants used in Step 3 can be obtained in any way known to the skilled person, such as obtained from a natural source, such as acquired commercially, such as synthesised using any route and starting materials.

The benzylamine can be a free amine or in the form of any suitable salt, such as a hydrochloride salt.

In preferred embodiments, the benzylamine (2) is vanillylamine hydrochloride (2a).

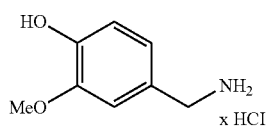

Step 3 is performed by addition of compound 3 to CDI to form the presumed carbonyl imidazole intermediate. In some embodiments, the addition of 3 is gradual, such as dropwise. The reaction is performed in any solvent or combination of two or more solvents that is understood by the skilled person to be suitable for the reaction may be used. In some embodiments, the solvent is selected from the list comprising, but not limited to, methyl tert-butyl ether (MTBE), tetrahydrofuran (THF), dichloromethane, acetonitrile, toluene, ethyl acetate, dimethylformamide (DMF) or any combination thereof. In certain embodiments, the solvent is MTBE. The solvent may be an anhydrous solvent.

In some embodiments, the reaction of Scheme 4 is performed at ambient temperature. In other embodiments, the reaction is performed at elevated temperatures, such as between 25° C. and the boiling point of the solvent, such as between 25° C. and 110° C., such as between 25° C. and 75° C., such as between 30° C. and 50° C., such as at 40° C. In some embodiments, the same reaction temperature is maintained throughout the course of the reaction. In other embodiments, the reaction temperature is varied and/or allowed to vary during the course of the reaction. In certain embodiments, the reaction mixture is heated after a time period at ambient temperature, such as to between 25° C. and 110° C., such as to between 25° C. and 75° C., such as to between 30° C. and 50° C., such as to 40° C.

In some embodiments, the reaction time before addition of or to compound 2 is decided based on when analysis of the reaction mixture shows that the reaction has proceeded to completion, or when analysis of the reaction mixture shows that the reaction has stopped. Any analytic method known to the skilled person may be used, such as a chromatographic method, such as thin layer chromatography, such as HPLC. In other embodiments, a set reaction time is used. In some embodiments, the reaction time is between 15 minutes and 3 hours, such as between 30 minutes and 2 hours, such as between 1 hour and 1 hour 45 minutes.

Compound 2 is added to the reaction mixture comprising compound 3 and CDI, or the reaction mixture comprising compound 3 and CDI is added to compound 2. In some embodiments, equimolar amounts of 2 and 3 are used. In other embodiments, an excess of 2 is used, such as 1.01-1.5 molar equivalents, such as 1.05-1.4 molar equivalents, such as 1.1-1.3 equivalents, based on the amount of 3. In yet other embodiments, an excess of 3 is used, such as 1.01-1.5 molar equivalents, such as 1.05-1.4 molar equivalents, such as 1.1-1.3 equivalents, based on the amount of 2.

In some embodiments, the reaction between 3 and 2 is performed at ambient temperature. In other embodiments, the reaction is performed at elevated temperatures, such as between 25° C. and the boiling point of the solvent, such as between 25° C. and 110° C., such as between 25° C. and 75° C., such as between 30° C. and 50° C., such as at 45° C. In some embodiments, the same reaction temperature is maintained throughout the course of the reaction. In other embodiments, the reaction temperature is varied and/or allowed to vary during the course of the reaction.

In some embodiments, the reaction mixture is quenched, such as by addition of water, such as with continued stirring at an elevated temperature after addition of water. Work-up of the reaction mixture may be performed by any method commonly used by the person skilled in the art. In some embodiments, a phase separation occurs. In certain embodiments, the desired product (1) is in the organic phase, and precipitated from this organic phase by methods commonly used by the person skilled in the art.

In some embodiments, the reaction mixture is quenched when analysis of the reaction mixture shows that the reaction has proceeded to completion, or when analysis of the reaction mixture shows that the reaction has stopped. Any analytic method known to the skilled person may be used, such as a chromatographic method, such as thin layer chromatography, such as HPLC. In other embodiments, the reaction mixture is quenched after a set reaction time, such as 2-50 hours, such as 5-40 hours, such as 10-25 hours, such as 15-20 hours, such as 15-30 hours.

In preferred embodiments of Step 3, Step 3 is performed by dropwise addition of compound 3 to CDI, and using MTBE as solvent and a reaction temperature between 25° C. and 50° C. Compound 2 may be vanillylamine, preferably vanillylamine hydrochloride (2a).

Step 2

In some embodiments, compound 3 is synthesised by reacting compound 4 with a dialkyl malonate (5) under basic conditions, such as via intermediate 3', as shown in Scheme 5. This step is referred to as Step 2.

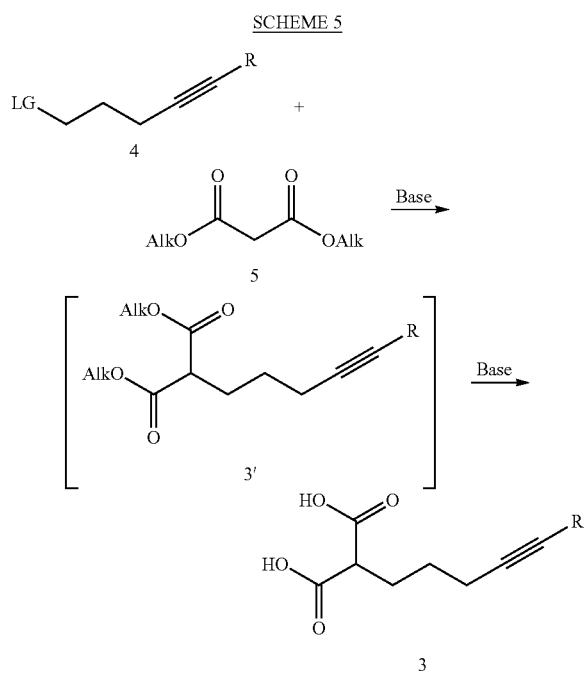

SCHEME 5

Alk in Scheme 5 denotes straight chained, branched or cyclic $C_1$-$C_6$ alkyl groups, so that compound 5 is a dialkyl-malonate. In some embodiments, the Alk groups are identical to each other. In some embodiments, both Alk groups are methyl, so that 5 is dimethyl malonate. In some embodiments, both Alk groups are ethyl, so that 5 is diethyl malonate.

The reactants used in Step 2 can be obtained in any way known to the skilled person, such as obtained from a natural source, such as acquired commercially, such as synthesised using any route and starting materials.

LG in Scheme 5 denotes any leaving group well known to the person skilled in the art. In some embodiments, LG is selected from the list comprising, but not limited to, perfluoroalkylsulfonates such as triflates; sulfonates such as tosylates, mesylates; and fluoro; chloro; bromo; and iodo. In some embodiments, LG is selected from fluoro, chloro, bromo, iodo, triflate, tosylate and mesylate. In some embodiments, LG is chloro.

The reaction of step 2, between compound 4 and dialkyl malonate 5, can be performed using any base commonly used by the skilled person for deprotonation of dialkyl malonates. In some embodiments, the base is selected from the list comprising, but not limited to, alkoxide bases, such as sodium methoxide, sodium ethoxide, sodium butoxide, such as sodium ethoxide in ethanol, such as sodium methoxide in methanol, and hydroxide bases, such as sodium hydroxide. In some embodiments, compound 5 is pre-treated with the base before the addition of compound 4, while in other embodiments, compound 5, base, and compound 4 are added simultaneously. In some embodiments, equimolar amounts of 5 and 4 are used. In other embodiments, an excess of the 4 is used, such as 1.01-1.5 molar equivalents, such as 1.05-1.4 molar equivalents, such as 1.1-1.3 molar equivalents based on the amount of 5. In yet other embodiments, an excess of the 5 is used, such as 1.01-1.5 molar equivalents, such as 1.05-1.4 molar equivalents, such as 1.1-1.3 molar equivalents based on the amount of 4.

Any solvent or combination of two or more solvents that is understood by the skilled person to be suitable for the reaction may be used. In some embodiments, the solvent is selected from the list comprising, but not limited to, methanol, ethanol, n-propanol, iso-propanol, tert-butanol, DMSO, DMF, THF, MTBE, toluene or any combination thereof. In certain embodiments, the solvent is methanol. In certain embodiments, the solvent is ethanol. The solvent may be an anhydrous solvent.

In some embodiments, the reaction between 4 and 5 is performed at ambient temperature. In other embodiments, the reaction is performed at elevated temperatures, such as between 25° C. and the boiling point of the solvent, such as between 25° C. and 78° C., such as between 40° C. and 75° C., such as between 60° C. and 75° C., such as at 70° C. In some embodiments, the same reaction temperature is maintained throughout the course of the reaction. In other embodiments, the reaction temperature is varied and/or allowed to vary during the course of the reaction. In some embodiments, the reaction mixture is quenched when analysis of the reaction mixture shows that the reaction has proceeded to completion, or when analysis of the reaction mixture shows that the reaction has stopped. Any analytic method known to the skilled person may be used, such as a chromatographic method, such as thin layer chromatography, such as HPLC. In other embodiments, the reaction mixture is quenched after a set reaction time, such as 10-70 hours, such as 20-60 hours, such as 30-50 hours, such as 40-50 hours. In some embodiments, the reaction mixture is quenched, such as at ambient temperature, such as by addition of water.

The resulting diester intermediate 3' is then transformed into the corresponding diacid compound 3.

In some embodiments, intermediate 3' is isolated before said transformation, using standard techniques known to the person skilled in the art. In preferred embodiments, intermediate 3' is not isolated.

In some embodiments, said transformation is achieved by addition of a base to compound 3', such as by addition of an aqueous base. In some embodiments, the base is selected from the list comprising, but not limited to, sodium hydroxide, lithium hydroxide, potassium hydroxide, rubidium hydroxide, caesium hydroxide, calcium hydroxide, strontium hydroxide, barium hydroxide. In certain embodiments, the base is sodium hydroxide. In some embodiments, the reagents are allowed to react until analysis of the reaction mixture shows that the reaction has proceeded to completion, or when analysis of the reaction mixture shows that the reaction has stopped. Any analytic method known to the skilled person may be used, such as a chromatographic method, such as thin layer chromatography, such as HPLC. In other embodiments, the reaction mixture is quenched after a set reaction time.

Work-up of the reaction mixture may be performed by any method commonly used by the person skilled in the art, such as by concentration under vacuum and re-dissolving, such as re-dissolving in water. In some embodiments, the mixture is extracted, such as after concentration and re-dissolving in water. In some embodiments, the resulting aqueous phase is added aqueous acid, such as HCl, until precipitation of the product. In other embodiments, the aqueous phase is acidified and the product extracted into an organic phase. In some embodiments, the product is washed. A solid product may be filtered and rinsed.

In preferred embodiments of Step 2, Step 2 is performed using diethyl malonate or dimethyl malonate and an alkoxide base, and the diester intermediate 3' is not isolated before treatment with aqueous sodium hydroxide to yield 3. LG may be chloro.

Step 1

In some embodiments, compound 4 is synthesised by treating compound 7 with a base and reacting it with a 1,3-substituted propane compound of general formula LG-CH$_2$—CH$_2$—CH$_2$-LG' (6) as shown in Scheme 6, wherein LG and LG' are leaving groups known to the skilled person. This step is referred to as Step 1. In preferred embodiments, LG and LG' are different leaving groups with different leaving group ability. In other embodiments, LG and LG' are identical.

SCHEME 6

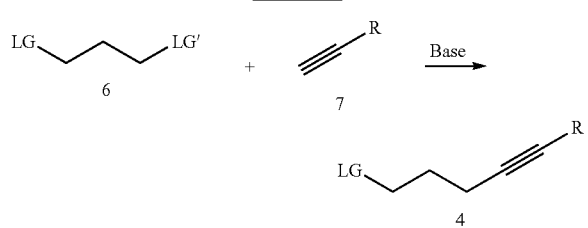

The reactants used in Step 1 can be obtained in any way known to the skilled person, such as obtained from a natural source, such as acquired commercially, such as synthesised using any route and starting materials.

In some embodiments, LG and LG' are different or identical leaving groups selected from the list comprising, but not limited to, perfluoroalkylsulfonates such as triflates; sulfonates such as tosylates, mesylates; fluoro, chloro, bromo, and iodo. In some embodiments, LG and LG' are selected from fluoro, chloro, bromo, iodo, triflate, tosylate and mesylate. In some embodiments, LG and LG' are both selected from chloro, bromo, and iodo. In preferred embodiments, LG and LG' are chloro and bromo, respectively, and thus 6 is 1-bromo-3-chloropropane.

In some embodiments, the base is selected from the list comprising, but not limited to, sodium hydride (NaH), normal-butyl lithium (n-BuLi), tert-butyl lithium (t-BuLi), lithium diisopropylamide (LDA), sodium amide (NaNH$_2$), lithium bis(trimethylsilyl)amide (((CH$_3$)$_3$Si)$_2$NLi). In some embodiments, the base is sodium hydride, such as sodium hydride in mineral oil. In some embodiments, compound 7 is pre-treated with the base before addition of compound 6, while in other embodiments, compound 7, base, and compound 6 are added simultaneously. In some embodiments, equimolar amounts of 7, base, and 6 are used. In other embodiments, an excess of base is used, such as 1.01-1.5 molar equivalents, such as 1.1-1.4 molar equivalents, such as 1.2-1.35 molar equivalents based on the amount of 7. In certain embodiments, an excess of 6 is used, such as 1.01-1.8 molar equivalents, such as 1.2-1.7 molar equivalents, such as 1.4-1.6 molar equivalents based on the amount of 7.

In some embodiments, particularly embodiments for which the skilled person would recognise the need for or advantage of this, anhydrous conditions are used.

Any solvent or combination of two or more solvents that is understood by the skilled person to be suitable for the reaction may be used. In some embodiments, the solvent is selected from the list comprising, but not limited to, THF, dichloromethane, N-methylpyrrolidone, MTBE, dioxane, 2-MeTHF, cyclopentyl methyl ether, DMSO, DMF or any combination thereof. In preferred embodiments, the solvent contains DMSO. In certain embodiments, the solvent is DMSO. In certain embodiments, the solvent is any mixture of THF and DMSO. The solvent may be an anhydrous solvent.

In some embodiments, the reaction is performed at ambient temperature. In other embodiments, the reaction is performed at temperatures below ambient temperature, such as between −78° C. and −20° C. In other embodiments, the reaction is performed at elevated temperatures, such as between 25° C. and the boiling point of the solvent, such as between 25° C. and 65° C., such as between 30° C. and 60° C., such as between 40° C. and 55° C., such as at 50° C. In some embodiments, the same reaction temperature is maintained throughout the course of the reaction. In other embodiments, the reaction temperature is varied and/or allowed to vary during the course of the reaction. In some embodiments, the reaction mixture is quenched when analysis of the reaction mixture shows that the reaction has proceeded to completion, or when analysis of the reaction mixture shows that the reaction has stopped. Any analytic method known to the skilled person may be used, such as a chromatographic method, such as thin layer chromatography, such as HPLC, such as GC. In other embodiments, the reaction mixture is quenched after a set reaction time, such as 2-50 hours, such as 5-40 hours, such as 10-25 hours, such as 15-20 hours, such as 15-30 hours.

In some embodiments, the reaction mixture is quenched, such as at ambient temperature, such as by addition of acid, such as by addition of water, such as by addition of an aqueous strong acid, such as addition by an aqueous weak acid. In some embodiments, the reaction is quenched by addition of an aqueous acid selected from the list comprising, but not limited to, hydrochloric acid, nitric acid, sulfuric acid, hydrobromic acid, hydroiodic acid, perchloric acid, and chloric acid.

Work-up of the reaction mixture may be performed by any method commonly used by the person skilled in the art, such as by separation of the two layers after a quench with an aqueous acid and/or by extraction of the organic phase. In some embodiments, the solvent from the organic phase is evaporated to yield the crude product. In some embodiments, the organic phase or the crude product is purified, such as by any method commonly used by the person skilled in the art. In some embodiments, the purification method is distillation. In certain embodiments, the purification method is distillation under reduced pressure, such as at 0.1-50 mmHg, such as at 30-50 mmHg, such as at 30-40 mmHg, such as at 10-40 mmHg, such as at 0.1-20 mmHg, such as at 1-10 mmHg, such as at 2-3 mmHg.

In preferred embodiments of Step 1, LG and LG' are both halogens, the base is sodium hydride, and the solvent contains DMSO. LG and LG' may be chloro and bromo, respectively.

In some embodiments, compound 1 is synthesised using Step 3, using reactants (3 and 2) obtained in any way known to the skilled person, such as obtained from a natural source, such as acquired commercially, such as synthesised using any route and starting materials. Preferably, Step 3 is performed by dropwise addition of compound 3 to CDI, and using MTBE as solvent and a reaction temperature between 25° C. and 50° C., and subsequent addition of benzylamine 2.

In other embodiments, compound 1 is synthesised using Steps 2 and 3, as illustrated in Scheme 7, using reactants (4 and 5) obtained in any way known to the skilled person, such as obtained from a natural source, such as acquired commercially, such as synthesised using any route and starting materials. Preferably, Step 2 is performed using diethyl malonate or dimethyl malonate and an alkoxide base, and the diester intermediate 3' is not isolated before treatment with aqueous sodium hydroxide to yield 3, and Step 3 is performed by dropwise addition of compound 3 to CDI, using MTBE as solvent and a reaction temperature between 25° C. and 50° C., and subsequent addition of benzylamine 2.

SCHEME 7

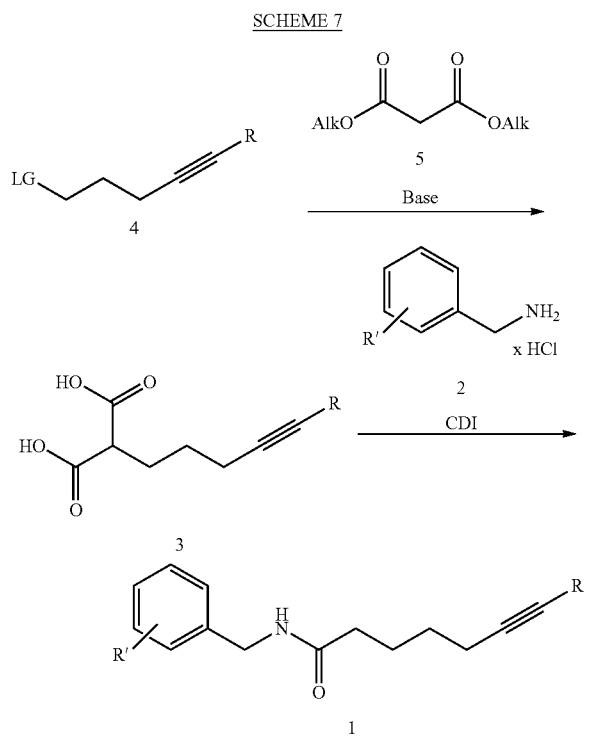

In yet other embodiments, compound 1 is synthesised using Steps 1, 2, and 3, as illustrated in Scheme 8. Preferably, in Step 1, LG and LG' are both halogens, the base is sodium hydride, and the solvent contains DMSO and THF; Step 2 is performed using diethyl malonate or dimethyl malonate and an alkoxide base, and the diester intermediate 3' is not isolated before treatment with sodium hydroxide to yield 3; and Step 3 is performed by dropwise addition of compound 3 to CDI, and using MTBE as solvent and a reaction temperature between 25° C. and 50° C., and subsequent addition of benzylamine 2.

SCHEME 8

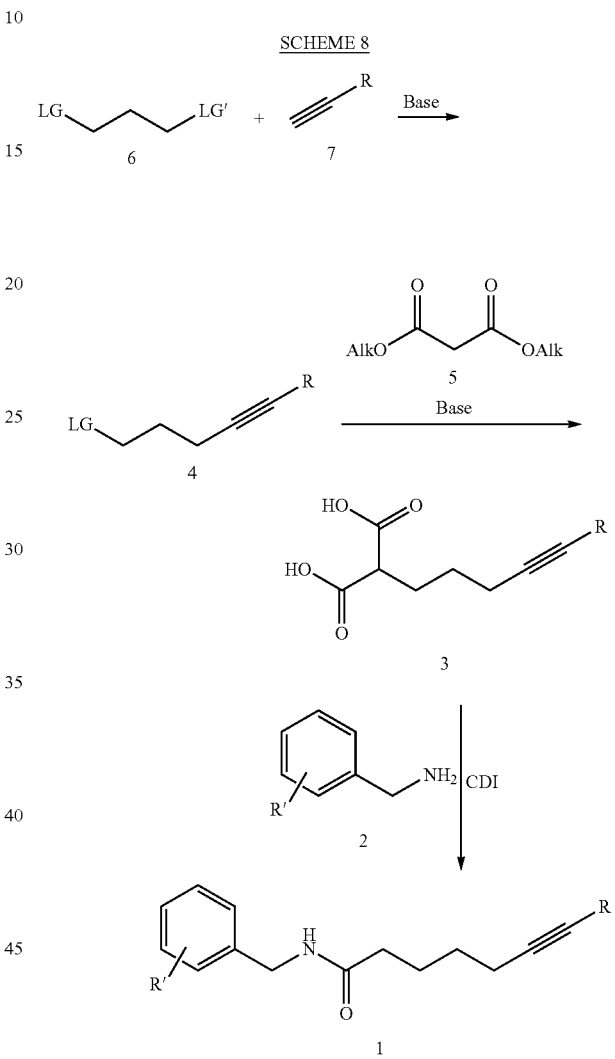

In some embodiments, the invention provides a synthetic route to capsaicyns with a complete vanillyl ring, of general structure 1V, as shown in Scheme 9. In such embodiments, compound 2 is vanillylamine, such as vanillylamine hydrochloride (2a). In certain embodiments, only step 3 is performed. In other embodiments, steps 2 and 3 are performed. In yet other embodiments, all steps 1-3 are performed.

Preferably, in Step 1 (if performed), LG and LG' are both halogens, the base is sodium hydride, and the solvent contains DMSO and THF; Step 2 (if performed) is performed using diethyl malonate or dimethyl malonate and an alkoxide base, and the diester intermediate 3' is not isolated before treatment with aqueous sodium hydroxide to yield 3; and Step 3 is performed by dropwise addition of compound 3 to CDI, and using MTBE as solvent and a reaction temperature between 25° C. and 50° C., and subsequent addition of benzylamine 2.

SCHEME 9

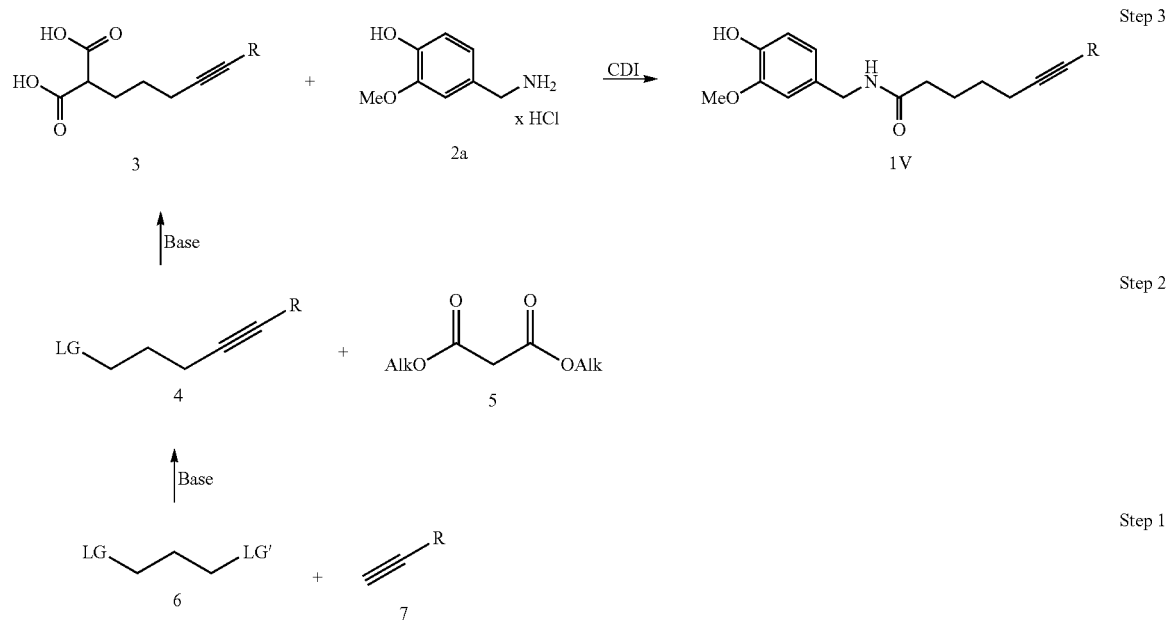

In some embodiments, the invention provides a synthetic route to phenylcapsaicyns of general structure 1P, as shown in Scheme 10. In such embodiments, compound 2 is vanillylamine, such as vanillylamine hydrochloride (2a) and substituent Ar is a phenyl ring or a substituted phenyl ring as described above. In certain embodiments, only step 3 is performed. In other embodiments, steps 2 and 3 are performed. In yet other embodiments, steps 1-3 are performed. Preferably, in Step 1 (if performed), LG and LG' are both halogens, the base is sodium hydride, and the solvent contains DMSO and THF; Step 2 (if performed) is performed using diethyl malonate or dimethyl malonate and an alkoxide base, and the diester intermediate 3' is not isolated before treatment with sodium hydroxide to yield 3; and Step 3 is performed by dropwise addition of compound 3 to CDI, and using MTBE as solvent and a reaction temperature between 25° C. and 50° C., and subsequent addition of benzylamine 2.

SCHEME 10

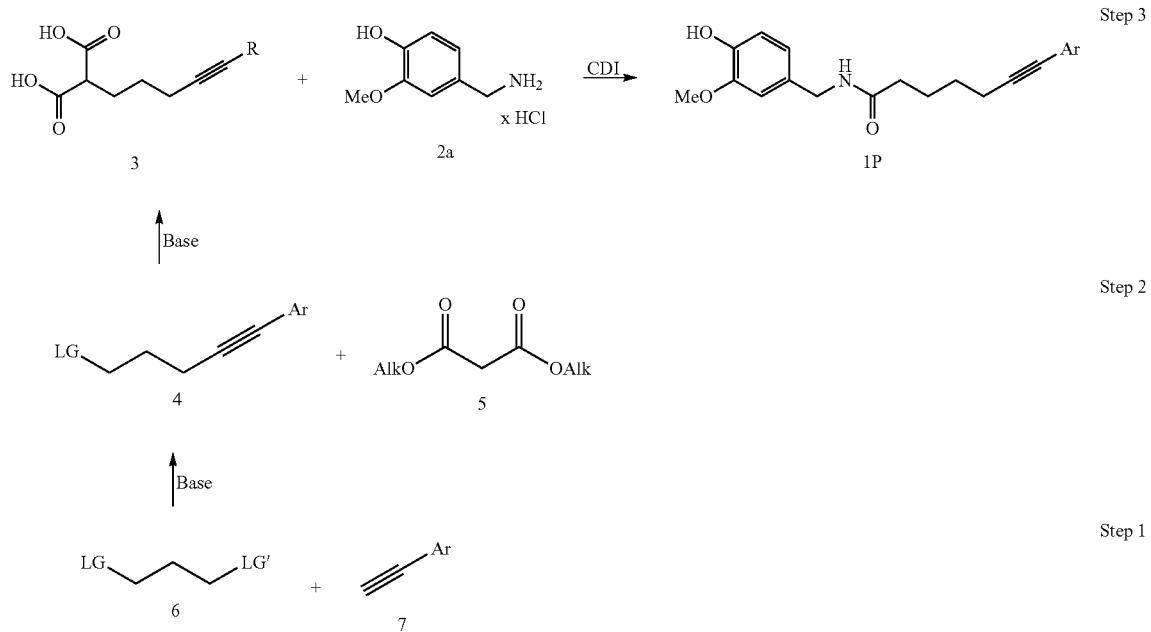

In specific embodiments, the invention provides a synthetic route to phenylcapsaicin (1a), as shown in Scheme 11. In such embodiments, compound 2 is vanillylamine hydrochloride, 2a, substituent Ph is an unsubstituted phenyl ring. In certain embodiments, only step 3 is performed. In other embodiments, steps 2 and 3 are performed. In yet other embodiments, steps 1-3 are performed.

Preferably, in Step 1 (if performed), LG and LG' are both halogens, the base is sodium hydride, and the solvent contains DMSO and THF; Step 2 (if performed) is performed using diethyl malonate or dimethyl malonate and an alkoxide base, and the diester intermediate 3' is not isolated before treatment with sodium hydroxide to yield 3; and Step 3 is performed by dropwise addition of compound 3 to CDI, and using MTBE as solvent and a reaction temperature between 25° C. and 50° C., and subsequent addition of benzylamine 2.

In a specific embodiment, 1a is crystallised by addition of water to a solution of 1a resulting directly from Step 3 after washing the organic phase with water, by addition of water and stirring with cooling to a temperature in the range from −5° C. to 5° C. for 5 hours.

It will be clear to the skilled person that the crystallisation method described for 1a, or similar methods, may also be used for other capsaicin derivatives.

The invention shall not be limited to the shown embodiments and examples. While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the scope of the present invention. It is to be understood that various alternatives to

SCHEME 11

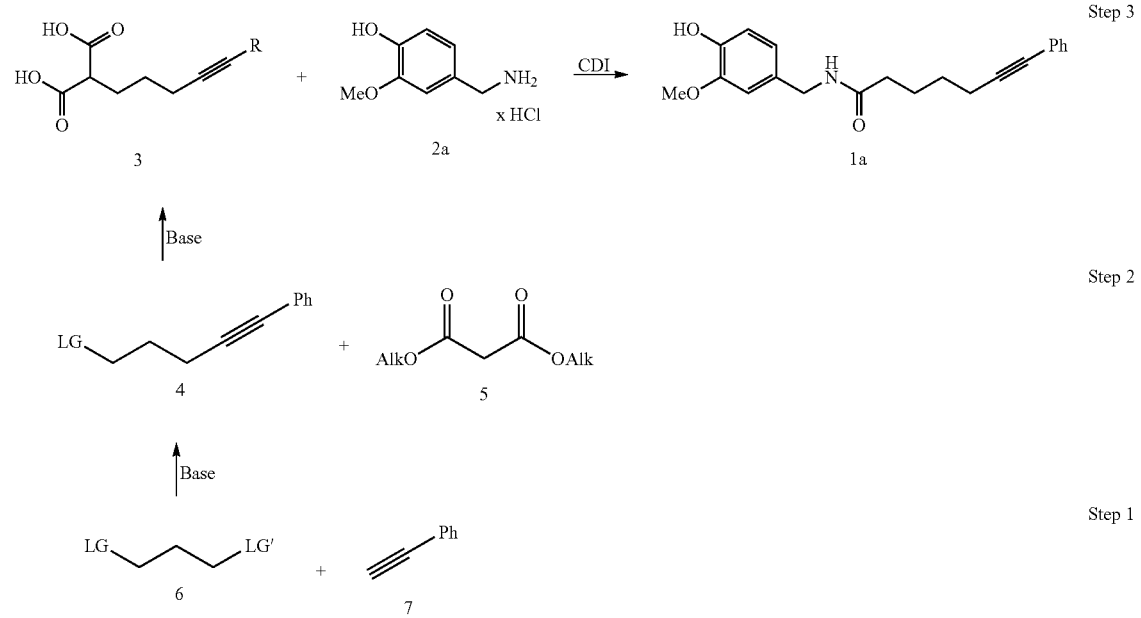

Crystallisation

All capsaicin derivatives synthesised according to the invention may be purified subsequent to their synthesis. In some embodiments, the capsaicin derivative is a solid compound. For such embodiments, the capsaicin derivative may be crystallised. In some embodiments, phenylcapsaicin (1a) is crystallised by addition of water to a solution of 1a in MTBE, such as a solution of 1a resulting directly from Step 3, optionally after washing the organic phase with water. The concentration of the solution may be 0.05-1 g/mL, such as 0.05-0.5 g/mL, such as 1-0.4 g/mL, such as 0.5-1 g/mL, such as 0.7-0.9 g/mL. The crystallisation is performed by addition of 0.25-1 volume of water per volume of solvent, such as 0.3-0.8, such as 0.4-0.7 volume of water per volume of solvent, and stirring with cooling to a temperature in the range from −5° C. to 5° C. for 2-24 hours, such as overnight, such as 3-6 hours, such as 5 hours, to give crystals of 1a. The crystals may be isolated, such as by filtration, and optionally rinsed with MTBE and dried, such as air dried.

the embodiments described herein can be employed in practicing the disclosure. Further, it is contemplated that the appended claims will cover such modifications and variations that fall within the true scope of the invention.

It is to be understood that every embodiment of the disclosure can optionally be combined with any one or more of the other embodiments described herein.

It is to be understood that each component, compound, or parameter disclosed herein is to be interpreted as being disclosed for use alone or in combination with one or more of each and every other component, compound, or parameter disclosed herein. It is further to be understood that each amount/value or range of amounts/values for each component, compound, or parameter disclosed herein is to be interpreted as also being disclosed in combination with each amount/value or range of amounts/values disclosed for any other component(s), compound(s), or parameter(s) disclosed herein, and that any combination of amounts/values or ranges of amounts/values for two or more component(s), compound(s), or parameter(s) disclosed herein are thus also disclosed in combination with each other for the purposes of this description. Any and all features described herein, and combinations of such features are included within the scope of the present invention provided that the features are not mutually inconsistent.

It is to be understood that each lower limit of each range disclosed herein is to be interpreted as disclosed in combination with each upper limit of each range disclosed herein for the same component, compound, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, or parameter disclosed in the description or an example is to be interpreted as a disclosure of either a lower or an upper limit of a range and thus can be combined with any other lower or upper limit or a range or specific amount/value for the same component, compound, or parameter disclosed elsewhere in the application to form a range for that component, compound, or parameter.

EXAMPLES

Phenylcapsaicin (1a) was synthesised according to the route shown in Scheme 12. The reactions were monitored by HPLC on a reverse phase (Phenomenex phenyl-C6) column with 80% methanol at pH 2 (0.1% TFA) as mobile phase, 1.5 ml/min. analysing at 240 nm. Products were identified through MS and/or NMR analysis.

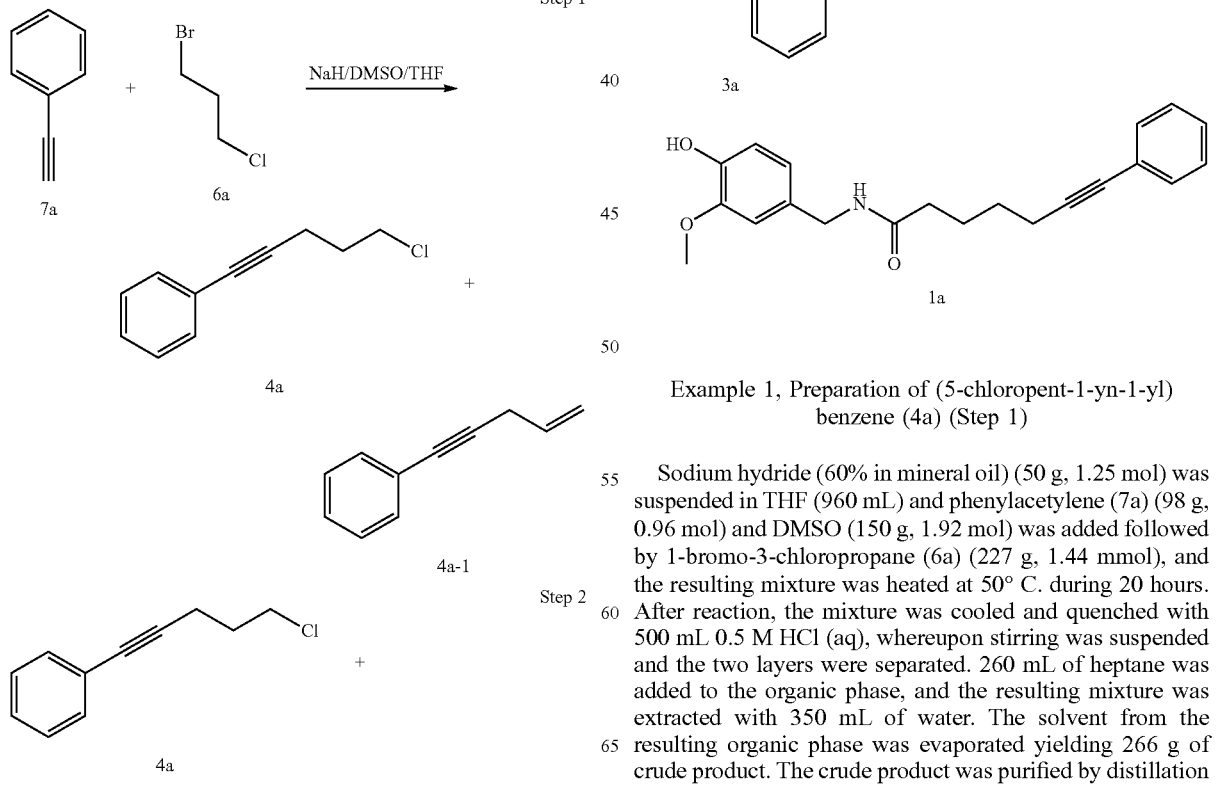

Example 1, Preparation of (5-chloropent-1-yn-1-yl) benzene (4a) (Step 1)

Sodium hydride (60% in mineral oil) (50 g, 1.25 mol) was suspended in THF (960 mL) and phenylacetylene (7a) (98 g, 0.96 mol) and DMSO (150 g, 1.92 mol) was added followed by 1-bromo-3-chloropropane (6a) (227 g, 1.44 mmol), and the resulting mixture was heated at 50° C. during 20 hours. After reaction, the mixture was cooled and quenched with 500 mL 0.5 M HCl (aq), whereupon stirring was suspended and the two layers were separated. 260 mL of heptane was added to the organic phase, and the resulting mixture was extracted with 350 mL of water. The solvent from the resulting organic phase was evaporated yielding 266 g of crude product. The crude product was purified by distillation at reduced pressure (2-3 mmHg), and the first fraction boiling at 30-40° C. containing the excess staring materials was separated. The main fraction boiling at 90-100° C. contained the product and a small amount of compound 4a-1, which has a slightly lower boiling point than 3. It is therefore difficult to remove, but as it is unreactive in the following step and completely removed after the hydrolysis, its presence can be tolerated. The yield of 4a was 146 g (85%) containing 1.5% of 4a-1 (by HPLC area) after distillation.

$^1$H NMR(DMSO-d6) δ 7.43-7.38 (m, 2H), 7.35-7.32 (m, 3H), 3.76 (t, 2H, J=6.4 Hz), 2.58 (t, 2H, J=7.0 Hz), 1.98 (p, 2H, J=6.7 Hz); $^{13}$C NMR(CDCl$_3$) δ 131.2, 128.4, 127.9, 123.0, 88.7, 81.1, 44.1, 31.0, 16.2.

Example 2, Preparation of 2-(5-phenylpent-4-yn-1-yl)malonic acid (3a) (Step 2)

Compound 3a was synthesised via intermediate 3'a (shown in Scheme 13 with only ethyl groups, but which contained a combination of ethyl and methyl groups due to transesterification), which was not isolated.

Diethyl malonate (5a) (184 g, 1.15 mol) and 4a (137 g, 0.767 mol) were dissolved in ethanol (430 mL), whereupon sodium methoxide (203 g 25% solution in methanol, 0.939 mol) was added. The mixture was heated at 70° C. for 48 hours. After cooling, the mixture was quenched with 290 mL water, and 333 g of 28% (aq.) sodium hydroxide solution was added and the reaction mixture was stirred at 30° C. until HPLC analysis showed complete conversion of the esters to the malonic acid derivative 3a.

The reaction mixture was concentrated under vacuum to a semi crystalline mass and re-dissolved in 550 mL water. The mixture was extracted twice with 300 mL portions of methyl-tert-butylether. To the resulting aqueous phase, 365 g 30% HCl was slowly added, whereupon the product precipitated. After stirring at 25° C. for 2 hours, the product was filtered, rinsed with 70 mL of heptane followed by 70 mL of water. The resulting product, 3a, was air dried to yield 164 g light tan crystals (87% yield).

$^1$H NMR(DMSO-d$_6$) δ 7.38-7.34 (m, 2H), 7.33-7.28 (m, 3H), 3.31 (t, 1H, J=7.6 Hz), 2.43 (t, 2H, J=6.9 Hz), 1.90-1.84 (m, 2H), 1.59-1.51 (m, 2H); $^{13}$C NMR(DMSO-d$_6$) δ 171.1, 131.4, 128.7, 128.1, 123.4, 90.3, 81.0, 51.4, 28.0, 26.3, 18.7. HRMS (ESI) calcd for C$_{14}$H$_{15}$O$_4^+$ [M+H]$^+$ 247.0970, found 247.0968.

Example 3, Preparation of Phenylcapsaicin (1a) (Step 3)

Malonic acid 3a, (130 g, 0.528 mol) was dissolved in 375 ml MTBE and added dropwise to a suspension of carbonyl-diimidazole (103 g, 0.635 mol) in 375 mL MTBE under gas evolution and the resulting mixture was stirred at 25° C. for 30 minutes and finally heated to 40° C. for an hour to drive the reaction to completion. To the mixture was added vanillylamine hydrochloride (2a), (120 g, 0.633 mol) and stirring was continued at 45° C. for 20 hours, whereupon 500 mL water was added and the mixture was stirred at 40° C. until two clear phases formed. The bottom aqueous layer was separated, and the organic phase was extracted again with 500 mL of water at 40° C. After separation 300 mL of water was added followed by 15 mL of HCl (30% aq.) and the layers separated.

Example 4, Crystallisation of Phenylcapsaicin (1a)

To the organic phase resulting from Example 3 was again added 300 mL of water and the mixture was stirred with cooling at 3° C. for 5 hours, resulting in precipitated product. The crystals were isolated by filtration and rinsed on the filter with 130 mL cold MTBE and air dried to provide 1a as a white crystalline material. The resulting solid was dissolved in 375 mL MTBE, whereupon the solvent was evaporated to yield 145 g, 81% yield, of 1a as a light brown syrup. $^1$H NMR(DMSO-d$_6$) δ 8.87 (s, 1H), 8.26 (t, 1H, J=5.7 Hz), 7.40-7.36 (m, 2H), 7.35-7.31 (m, 3H), 6.83 (d, 1H, J=1.7 Hz), 6.73 (d, 1H, J=7.9 Hz), 6.67 (dd, 1H, J=7.9, 1.7 Hz), 4.19 (d, 2H, J=5.7 Hz), 3.73 (s, 3H), 2.43 (t, 2H, J=7.0 Hz), 2.20 (t, 2H, J=7.2 Hz), 1.74-1.66 (m, 2H), 1.59-1.51 (m, 2H); $^{13}$C NMR(DMSO-d$_6$) δ 172.0, 147.5, 145.5, 131.3, 130.6, 128.6, 128.0, 123.4, 119.8, 115.3, 111.6, 90.5, 80.8, 55.5, 42.0, 35.0, 27.9, 24.8, 18.5. HRMS (ESI) calcd for C$_{21}$H$_{24}$NO$_3^+$ [M+H]$^+$ 338.1756, found 338.1759.

Capsaicyns 1b and 1c were synthesised according to the route shown in Scheme 13. Products were identified through MS and/or NMR analysis.

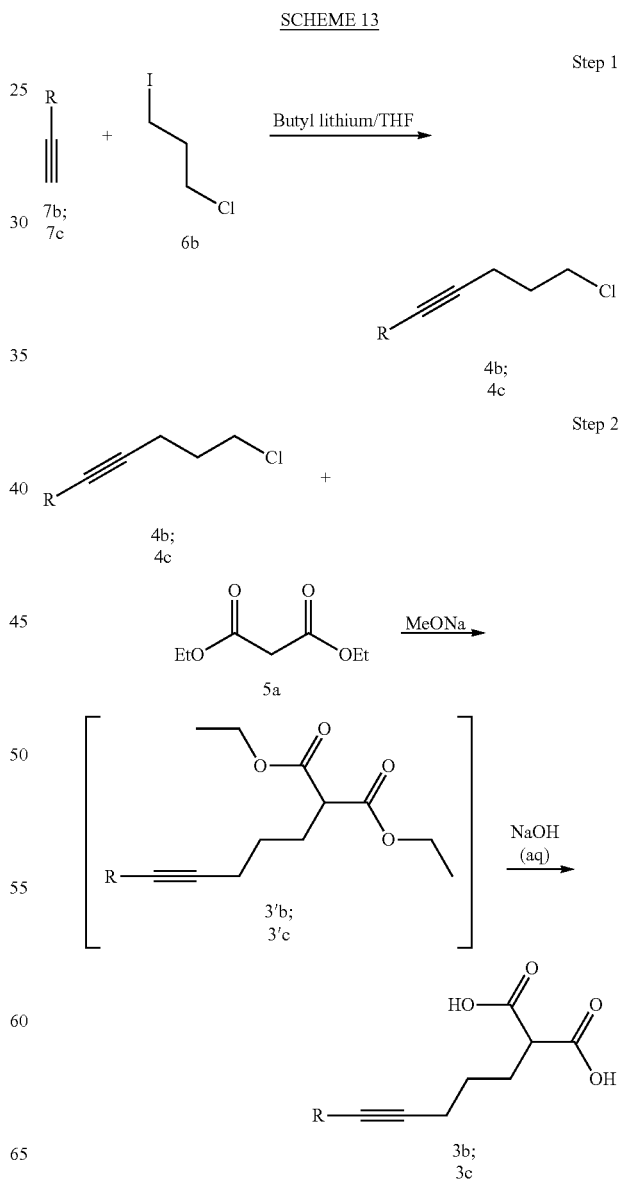

SCHEME 13

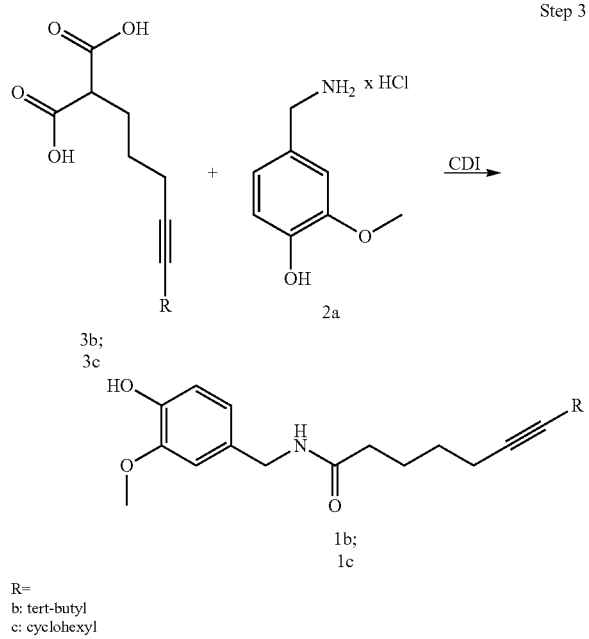

R=
b: tert-butyl
c: cyclohexyl

Example 5, Preparation of 7-chloro-2,2-dimethyl-3-heptyne (4b) (Step 1)

3,3-Dimethyl-1-butyne (7b) (3 g, 36.5 mmol) was dissolved in 27 ml anhydrous THF and the resulting mixture was cooled to −15° C. 1.6M Butyl lithium in hexanes (22.83 ml, 36.5 mmol) was added dropwise during 40 min, whereupon the mixture was allowed to reach 20° C. for 2 hours. 1-Chloro-3-iodopropane (6b) (6.35 g, 31.0 mmol) was added and the mixture was stirred at 20° C. for 3 days, whereupon 21 ml water was added. The bottom aqueous phase was removed, and a mixture of 10 ml water and 1 ml 25% HCl was added to the organic phase. The bottom aqueous phase was removed and the solvent from the organic phase was evaporated under reduced pressure to give a yellow oil (4b) (4.68 g, 29.5 mmol), in 95% yield. $^1$H NMR(CDCl$_3$) δ 3.63 (t, 2H, J=6.5 Hz), 2.31 (t, 2H, J=6.8 Hz), 1.91 (p, 2H, J=6.6 Hz), 1.18 (s, 9H); $^{13}$C NMR(CDCl$_3$) δ 90.1, 76.3, 43.8, 31.9, 31.3, 27.3, 16.2.

Example 6, Preparation of (3b) (6,6-dimethyl-4-heptynyl)malonic acid (Step 2)

Mix 7-chloro-2,2,-dimethyl-3-heptyne (4b) (4.12 g, 26.0 mmol), diethyl malonate (5a) (6.24 g, 38.9 mmol), ethanol (12.6 ml) and 25% sodium methanolate (7.01 g, 32.5 mmol). The mixture was heated at 70° C. for 3 days. After cooling, the mixture was quenched with 5.7 mL water, and 11.95 g of 28% (aq.) sodium hydroxide solution was added and the reaction mixture was stirred at 30° C. for 24 hours. The reaction mixture was concentrated under vacuum to a semi crystalline mass and re-dissolved in 16 mL water. The mixture was extracted twice with 10 mL portions of toluene. To the resulting aqueous phase, 16 g 25% HCl was added and the resulting mixture was extracted twice with 25 ml portions of MTBE. The MTBE portions were combined and the solvent was evaporated under reduced pressure to give an off-white solid (3b) (5.26 g, 23.3 mmol) in 90% yield.

$^1$H NMR(DMSO-d$_6$) δ 3.21 (t, 1H, J=7.3 Hz), 2.09 (t, 2H, J=7.2 Hz), 1.78-1.72 (m, 2H), 1.41-1.34 (m, 2H), 1.12 (s, 9H); $^{13}$C NMR(DMSO-d$_6$) δ 171.2, 89.6, 78.4, 51.6, 31.6, 28.1, 27.4, 26.8, 18.2. HRMS (ESI) calcd for C$_{12}$H$_{17}$O$_4^-$ [M−H]$^-$ 225.1127, found 225.1126.

Example 7, Preparation of (1b) N-[(4-hydroxy-3-methoxyphenyl)methyl]-8,8-dimethyl-6-nonynamide (Step 3)

(6,6-Dimethyl-4-heptynyl)malonic acid (3b) (1.0 g, 4.4 mmol) was dissolved in 5 ml MTBE and added dropwise to a suspension of carbonyldiimidazole (0.86 g, 5.3 mmol) in 5 mL MTBE under gas evolution and the resulting mixture was heated at 40° C. for an hour. The resulting solution was added to a suspension of vanillylamine hydrochloride (2a) (1.01 g, 5.3 mmol) and stirring was continued at 50° C. for 22 hours, whereupon 10 mL water was added and the mixture was stirred at 40° C. until two clear phases formed. The bottom aqueous layer was separated, and the organic phase was washed with a mixture of 10 mL water and 1 mL 25% HCl. The organic phase was extracted with a solution of 0.26 g sodium hydroxide and 10 ml water, and then further washed with 5 ml water. The two aqueous phases were combined and 0.6 mL 37% HCl (aq.) and 10 mL MTBE were added. The resulting aqueous phase was removed, and the organic phase was washed with 5 ml water. The solvent from the organic phase was removed under reduced pressure to give a yellow oil (1 b) (0.70 g, 2.2 mmol) in 50% yield. $^1$H NMR(CDCl$_3$) δ 6.86 (d, 1H, J=8.0 Hz), 6.79 (d, 1H, J=2.0 Hz), 6.74 (dd, 1H, J=8.0, 2.0 Hz), 4.34 (d, 2H, J=5.6 Hz), 3.86 (s, 3H), 2.22 (t, 2H, J=7.5 Hz), 2.15 (t, 2H, J=7.1 Hz), 1.77-1.70 (m, 2H), 1.54-1.46 (m, 2H), 1.16 (s, 9H); $^{13}$C NMR(CDCl$_3$) δ 172.7, 146.7, 145.1, 130.2, 120.8, 114.4, 110.7, 89.4, 77.8, 55.9, 43.6, 36.2, 31.4, 28.6, 27.3, 24.9, 18.4. HRMS (ESI) calcd for C$_{19}$H$_{28}$NO$_3^+$ [M+H]$^+$ 318.2069, found 318.2068.

Example 8, Preparation of 5-chloro-1-cyclohexyl-1-pentyne (4c) (Step 1)

Cyclohexylacetylene (7c) (2.46 g, 22.7 mmol) was dissolved in 22 ml anhydrous THF and the resulting mixture was cooled to −15° C. 1.6M Butyl lithium in hexanes (14.19 ml, 22.7 mmol) was added dropwise during 30 min, whereupon the mixture was allowed to reach 20° C. for 2 hours. 1-Chloro-3-iodopropane (6b) (3.95 g, 19.3 mmol) was added and the mixture was stirred at 20° C. for 3 days, whereupon 17 ml water was added. The bottom aqueous phase was removed, and a mixture of 10 ml water and 1 ml 25% HCl was added to the organic phase. The bottom aqueous phase was removed and the solvent from the organic phase was evaporated under reduced pressure to give a yellow oil (4c) (3.35 g, 18.2 mmol), in a 94% yield. $^1$H NMR(CDCl$_3$) δ 3.63 (t, 2H, J=6.5 Hz), 2.35-2.27 (m, 3H), 1.91 (p, 2H, J=6.6 Hz), 1.78-1.72 (m, 2H), 1.70-1.62 (m, 2H), 1.51-1.47 (m, 1H), 1.41-1.33 (m, 2H), 1.32-1.23 (m, 3H); $^{13}$C NMR(CDCl$_3$) δ 85.7, 77.8, 43.8, 33.1, 31.9, 29.1, 25.9, 24.9, 16.2.

Example 9, Preparation of (5-cyclohexyl-4-pentynyl)malonic acid (3c) (Step 2)

Mix 5-chloro-1-cyclohexyl-1-pentyne (4c) (1.97 g, 10.7 mmol), diethyl malonate (5a) (2.56 g, 16.0 mmol), ethanol (6.0 ml) and 25% sodium methanolate (2.88 g, 13.3 mmol). The mixture was heated at 70° C. for 2 days. After cooling, the mixture was quenched with 2.7 mL water, and 4.77 g of 28% (aq.) sodium hydroxide solution was added and the reaction mixture was stirred at 30° C. for 24 hours. The reaction mixture was concentrated under vacuum to a semi crystalline mass and re-dissolved in 40 mL water. The mixture was extracted twice with 25 mL portions of toluene. To the resulting aqueous phase, 6.5 g 25% HCl was added and the resulting mixture was extracted twice with 25 ml portions of MTBE. The MTBE portions were combined and the solvent was evaporated under reduced pressure to give an off-white solid (3c) (2.01 g, 8.0 mmol) in a 75% yield.
$^1$H NMR(CDCl$_3$) δ 3.48 (t, 1H, J=7.4 Hz), 2.33-2.28 (1H, m), 2.23 (dt, 2H, J=6.9, 2.2 Hz), 2.09-2.03 (m; 2H), 1.79-1.73 (m, 2H), 1.70-1.64 (m, 2H), 1.62-1.55 (m, 2H), 1.52-1.46 (m, 1H), 1.42-1.34 (m, 2H), 1.30-1.24 (m, 3H). $^{13}$C NMR(CDCl$_3$) δ 174.6, 85.7, 78.5, 51.1, 33.0, 29.1, 27.8, 26.6, 25.9, 24.9, 18.4. HRMS (ESI) calcd for C$_{14}$H$_{19}$O$_4^-$ [M–H]$^-$ 251.1283, found 251.1286.

Example 10, Preparation of N-[(4-hydroxy-3-methoxyphenyl)methyl]-7-cyclohexyl-6-heptynamide (1c) (Step 3)

(5-Cyclohexyl-4-pentynyl)malonic acid (3c) (1.0 g, 4.0 mmol) was dissolved in 5 mL MTBE and added dropwise to a suspension of carbonyldiimidazole (0.77 g, 4.8 mmol) in 5 mL MTBE under gas evolution and the resulting mixture was heated at 40° C. for an hour. The resulting solution was added to a suspension of vanillylamine hydrochloride (2a) (0.90 g, 4.8 mmol) and stirring was continued at 50° C. for 22 hours, whereupon 10 mL water was added and the mixture was stirred at 40° C. until two clear phases formed. The bottom aqueous layer was separated, and the organic phase was washed with a mixture of 10 mL water and 0.5 mL 25% HCl. The organic phase was extracted with a solution of 0.19 g sodium hydroxide and 10 mL water, and then further washed with 5 mL water. The two aqueous phases were combined and 0.43 mL 37% HCl (aq.) and 10 mL MTBE were added. The resulting aqueous phase was removed, and the organic phase was washed with 5 ml water. The solvent from the organic phase was removed under reduced pressure to give a yellow oil (1c) (0.68 g, 2.0 mmol) in 50% yield. $^1$H NMR(CDCl$_3$) δ 6.84 (d, 1H, J=8.0 Hz), 6.79 (d, 1H, J=2.0 Hz), 6.74 (dd, 1H, J=8.0, 2.0 Hz), 4.34 (d, 2H, J=5.5 Hz), 3.86 (s, 3H), 2.26-2.15 (m, 5H), 1.78-1.62 (m, 6H), 1.55-1.47 (m, 3H), 1.36-1.21 (m, 5H); $^{13}$C NMR (CDCl$_3$) δ 172.7, 146.7, 145.1, 130.2, 120.8, 114.4, 110.7, 85.2, 79.3, 55.9, 43.5, 36.2, 33.1, 29.1, 28.6, 25.9, 25.0, 24.9, 18.5. HRMS (ESI) calcd for C$_{21}$H$_{30}$NO$_3^+$[M+H]$^+$ 344.2226, found 344.2226.

ILLUSTRATIVE EXAMPLES

Illustrative Example I, Preparation of N-(4-hydroxy-3-methoxy)-nondec-6-ynamide

Sodium hydride (60% in mineral oil) is suspended in THF and dodecylacetylene and DMSO is added followed by 1-bromo-3-chloropropane (6a), and the resulting mixture is heated at 50° C. during 20 hours. After reaction, the mixture is cooled and quenched with 0.5 M HCl (aq), whereupon stirring is suspended and the two layers separated. Heptane is added to the organic phase, and the resulting mixture is extracted with water. The solvent from the resulting organic phase is evaporated yielding the crude product. The crude product is purified by short path distillation at reduced pressure.

The isolated intermediate and diethyl malonate (5a) are dissolved in ethanol, whereupon sodium methoxide (25% solution in methanol) is added. The mixture is heated at 70° C. for 48 hours. After cooling, the mixture is quenched with water, and 28% (aq.) sodium hydroxide solution is added, and the reaction mixture is stirred at 30° C. until HPLC analysis shows complete conversion of the esters to the malonic acid derivative 3. The reaction mixture is concentrated under vacuum to a semi crystalline mass and re-dissolved in water. The mixture is extracted twice with toluene. To the resulting aqueous phase, 30% HCl is slowly added, whereupon the product precipitates. After stirring at 25° C. for 2 hours, the product is filtered, and rinsed with heptane and water. The resulting malonic acid intermediate is air dried.

The malonic acid intermediate is dissolved in MTBE and added dropwise to a suspension of carbonyldiimidazole in MTBE and stirred at 25° C. for 30 minutes and finally heated to 40° C. for an hour to drive the reaction to completion. To the mixture is added vanillylamine hydrochloride and stirring is continued at 45° C. for 20 hours, whereupon water is added and the mixture is stirred at 40° C. until two phases form. The bottom aqueous layer is separated, and the organic phase is extracted again with water at 40° C. After separation 300 mL of water is added followed by 15 mL of HCl (30% aq.) and the layers separated. To the resulting organic phase is added 300 mL of water and the layers separated. To the resulting organic phase is added 20 g of magnesium sulphate. The mixture is stirred and filtered, and the solvent evaporated from the resulting filtrate to yield N-(4-dodecylbenzyl)-7-phenylhept-6-ynamide.

Illustrative Example II, Preparation of N-(4-hydroxy-3-methoxybenzyl)-8-methylnon-6-ynamide Sodium hydride (60% in mineral oil) is suspended in THF and 3-methyl-1-butyne and DMSO is added followed by 1-bromo-3-chloropropane (6a), and the resulting mixture is heated at 50° C. during 20 hours. After reaction, the mixture is cooled and quenched with 0.5 M HCl (aq), whereupon stirring is suspended and the two layers separated. Heptane is added to the organic phase, and the resulting mixture is extracted with water. The solvent from the resulting organic phase is evaporated yielding the crude product. The crude product is purified by distillation at reduced pressure.

The isolated intermediate and diethyl malonate (5a) are dissolved in ethanol, whereupon sodium methoxide (25% solution in methanol) is added. The mixture is heated at 70° C. for 48 hours. After cooling, the mixture is quenched with water, and 28% (aq.) sodium hydroxide solution is added, and the reaction mixture is stirred at 30° C. until HPLC analysis shows complete conversion of the esters to the malonic acid derivative 3. The reaction mixture is concentrated under vacuum to a semi crystalline mass and re-dissolved in water. The mixture is extracted twice with toluene. To the resulting aqueous phase, 30% HCl is slowly added, whereupon the product precipitates. After stirring at 25° C. for 2 hours, the product is filtered, and rinsed with heptane and water. The resulting malonic acid intermediate is air dried.

The malonic acid intermediate is dissolved in MTBE and added dropwise to a suspension of carbonyldiimidazole in MTBE and stirred at 25° C. for 30 minutes and finally heated to 40° C. for an hour to drive the reaction to completion. To the mixture is added vanillylamine hydrochloride and stirring is continued at 45° C. for 20 hours, whereupon water is added and the mixture is stirred at 40° C. until two phases form. The bottom aqueous layer is separated, and the organic phase is extracted again with water at 40° C. After separation 300 mL of water is added followed by 15 mL of HCl (30% aq.) and the layers separated. To the resulting organic phase is added 300 mL of water and the layers separated. To the resulting organic phase is added 20 g of magnesium sulphate. The mixture is stirred and filtered, and the solvent evaporated from the resulting filtrate to yield N-(4-hydroxy-3-methoxybenzyl)-8-methylnon-6-ynamide.

Illustrative Example III, Preparation of N-(3-fluoro-4-methoxybenzyl)-7-phenylhept-6-ynamide Sodium hydride (60% in mineral oil) is suspended in THF and phenylacetylene and DMSO is added followed by 1-bromo-3-chloropropane (6a), and the resulting mixture is heated at 50° C. during 20 hours. After reaction, the mixture is cooled and quenched with 0.5 M HCl (aq), whereupon stirring is suspended and the two layers separated. Heptane is added to the organic phase, and the resulting mixture is extracted with water. The solvent from the resulting organic phase is evaporated yielding the crude product. The crude product is purified by distillation at reduced pressure.

The isolated intermediate and diethyl malonate (5a) are dissolved in ethanol, whereupon sodium methoxide (25% solution in methanol) is added. The mixture is heated at 70° C. for 48 hours. After cooling, the mixture is quenched with water, and 28% (aq.) sodium hydroxide solution is added, and the reaction mixture is stirred at 30° C. until HPLC analysis shows complete conversion of the esters to the malonic acid derivative 3a. The reaction mixture is concentrated under vacuum to a semi crystalline mass and re-dissolved in water. The mixture is extracted twice with toluene. To the resulting aqueous phase, 30% HCl is slowly added, whereupon the product precipitates. After stirring at 25° C. for 2 hours, the product is filtered, and rinsed with heptane and water. The resulting malonic acid intermediate is air dried.

The malonic acid intermediate is dissolved in MTBE and added dropwise to a suspension of carbonyldiimidazole in MTBE and stirred at 25° C. for 30 minutes and finally heated to 40° C. for an hour to drive the reaction to completion. To the mixture is added 3-fluoro-4-methoxybenzylamine and stirring is continued at 45° C. for 20 hours, whereupon water is added and the mixture is stirred at 40° C. until two phases form. The bottom aqueous layer is separated, and the organic phase is extracted again with water at 40° C. After separation 300 mL of water is added followed by 15 mL of HCl (30% aq.) and the layers separated. To the resulting organic phase is added 300 mL of water and the layers separated. To the resulting organic phase is added 20 g of magnesium sulphate. The mixture is stirred and filtered, and the solvent evaporated from the resulting filtrate to yield N-(3-fluoro-4-methoxybenzyl)-7-phenylhept-6-ynamide.

The invention claimed is:
1. A method of preparing a 6-heptyne derivative of capsaicin of the following formula 1,

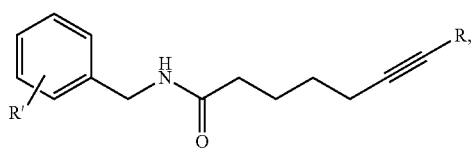

wherein:
R is a substituent selected from the group consisting of a $C_1$-$C_{18}$ straight chain or branched alkyl, a $C_2$-$C_{18}$ straight chain or branched alkenyl, a $C_2$-$C_{18}$ straight chain or branched alkynyl, trifluoromethyl, a $C_3$-$C_{12}$ cycloalkyl, phenoxy, phenylthiol, fluoro, chloro, bromo, iodo and an optionally substituted phenyl ring;
wherein the optionally substituted phenyl ring is optionally substituted in any position with 1-5 identical or different substituents selected from the group consisting of fluoro, chloro, bromo, iodo, cyano, nitro, trifluoromethyl, a $C_1$-$C_6$ straight chain or branched alkoxy, a $C_1$-$C_6$ sulfoxy, a —S—$C_1$-$C_6$ alkyl, a $C_1$-$C_6$ straight chain or branched alkyl, a $C_2$-$C_6$ straight chain or branched alkenyl, a $C_2$-$C_6$ straight chain or branched alkynyl, a $C_1$-$C_6$ fluoroalkyl, a $C_1$-$C_6$ chloroalkyl, a $C_1$-$C_6$ bromoalkyl, a $C_1$-$C_6$ iodoalkyl, a COO—$C_1$-$C_6$ alkyl, a CONH($C_1$-$C_6$ alkyl) and a CON($C_1$-$C_6$ alkyl)$_2$; and
R' is 0-5 identical or different substituents, in any one or more positions, selected from the group consisting of fluoro, chloro, bromo, iodo, hydroxy, cyano, amino, nitro, trifluoromethyl, a $C_1$-$C_6$ straight chain or branched alkoxy, a $C_1$-$C_6$ sulfoxy, a —S—$C_1$-$C_6$ alkyl, a $C_1$-$C_6$ straight chain or branched alkyl, a $C_2$-$C_6$ straight chain or branched alkenyl, a $C_2$-$C_6$ straight chain or branched alkynyl, a $C_1$-$C_6$ fluoroalkyl, a $C_1$-$C_6$ chloroalkyl, a $C_1$-$C_6$ bromoalkyl, a $C_1$-$C_6$ iodoalkyl, COOH, CONH$_2$, a —NHCO($C_1$-$C_6$ alkyl), a COO—$C_1$-$C_6$ alkyl, a CONH($C_1$-$C_6$ alkyl) and a CON($C_1$-$C_6$ alkyl)$_2$;
the method comprising a step of:
coupling a compound of the following formula 3 with a benzylamine of the following formula 2 or any suitable salt thereof, wherein R and R' in formula 2 and formula 3 are as defined in formula 1,

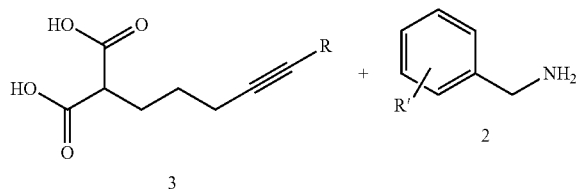

using 1,1'-carbonyldiimidazole (CDI).
2. The method according to claim 1, wherein R' is 0-5 identical or different substituents, in any one or more positions, selected from the group consisting of hydroxy, methoxy, fluoro, chloro, bromo and iodo.
3. The method according to claim 1, wherein R is selected from the group consisting of a $C_1$-$C_{18}$ is straight chain or branched alkyl, a $C_2$-$C_{18}$ straight chain or branched alkenyl, a $C_2$-$C_{18}$ straight chain or branched alkynyl and an optionally substituted phenyl ring.
4. The method according to claim 1, wherein R is a substituted phenyl ring which is substituted in any one or more positions with 1-5 identical or different substituents selected from the group consisting of fluoro, chloro, bromo, and iodo, or R is a $C_1$-$C_{12}$ straight chain or branched alkyl, a $C_2$-$C_{12}$ straight chain or branched alkenyl, a $C_2$-$C_{12}$ straight chain or branched alkynyl and a $C_1$-$C_6$ straight chain or branched alkoxy.
5. The method according to claim 4, wherein the substituted phenyl ring is mono, di or trisubstituted.

6. The method according to claim 1, wherein the method further comprises, before the coupling step, a step of reacting a compound of the following formula 4 with an alkyl malonate of the following formula 5, wherein R in the formula 4 is as defined in formula 3, to yield the compound of the formula 3;

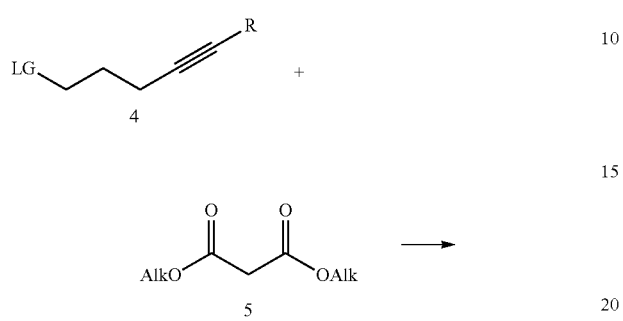

and
wherein
Alk is a straight chain, branched or cyclic $C_1$-$C_6$ alkyl group, and
LG is a leaving group.

7. The method according to claim 6, wherein LG is chloro.

8. The method according to claim 6, wherein the method further comprises, before the reacting step, a step of treating an ethynyl compound of the following formula 7 with a base and then reacting the compound of formula 7 and a 1,3-substituted propane compound of the following formula 6, wherein R in formula 7 is as defined in formula 4 to yield the compound of the formula 4,

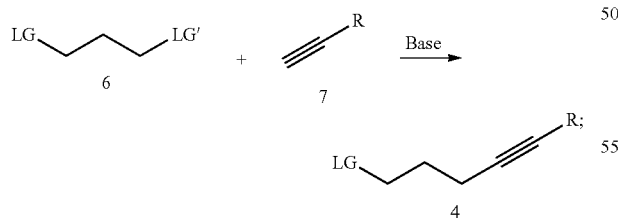

wherein LG and LG' are each an identical or different leaving group selected from the group consisting of a perfluoroalkylsulfonate, a sulfonate, fluoro, chloro, bromo and iodo.

9. The method according to claim 8, wherein LG and LG' are each selected from the group consisting of chloro, bromo and iodo.

10. The method according to claim 1, wherein the 6-heptyne derivative of capsaicin is a compound of the following formula 1V,

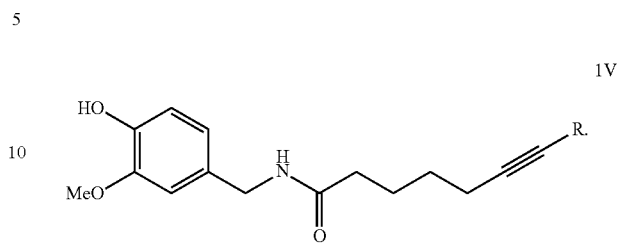

11. The method according to claim 1, wherein the 6-heptyne derivative of capsaicin is a compound of the following formula 1P,

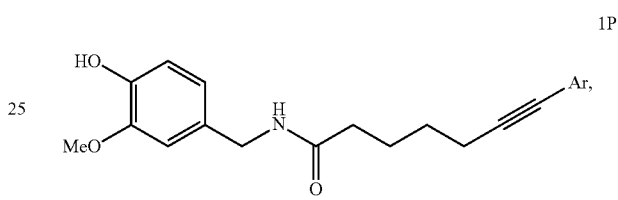

wherein Ar is a phenyl ring optionally substituted in any position with 1-5 identical or different substituents selected from the group consisting of fluoro, chloro, bromo, iodo, cyano, nitro, trifluoromethyl, a $C_1$-$C_6$ straight chain or branched alkoxy, a $C_1$-$C_6$ sulfoxy, a —S—$C_1$-$C_6$ alkyl, a $C_1$-$C_6$ straight chain or branched alkyl, a $C_2$-$C_6$ straight chain or branched alkenyl, a $C_2$-$C_6$ straight chain or branched alkynyl, a $C_1$-$C_6$ fluoroalkyl, a $C_1$-$C_6$ chloroalkyl, a $C_1$-$C_6$ bromoalkyl, a $C_1$-$C_6$ iodoalkyl, a COO—$C_1$-$C_6$ alkyl, a CONH($C_1$-$C_6$ alkyl) and a CON($C_1$-$C_6$ alkyl)$_2$.

12. The method according to claim 1, wherein the 6-heptyne derivative of capsaicin is phenylcapsaicin of the following formula (1a),

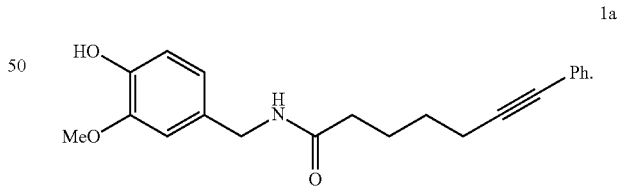

13. The method according to claim 12, which comprises preparing the phenylcapsaicin of formula (1a) from compound (6a) and compound (7a) according to the following reaction scheme:

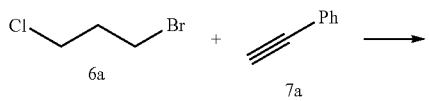

-continued

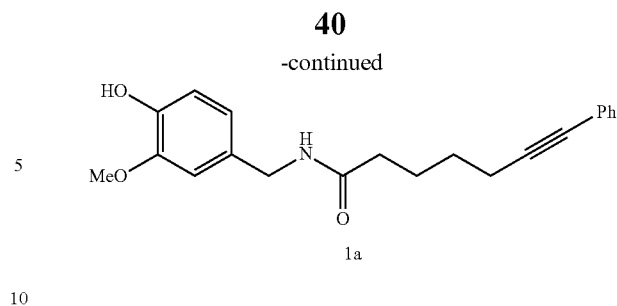

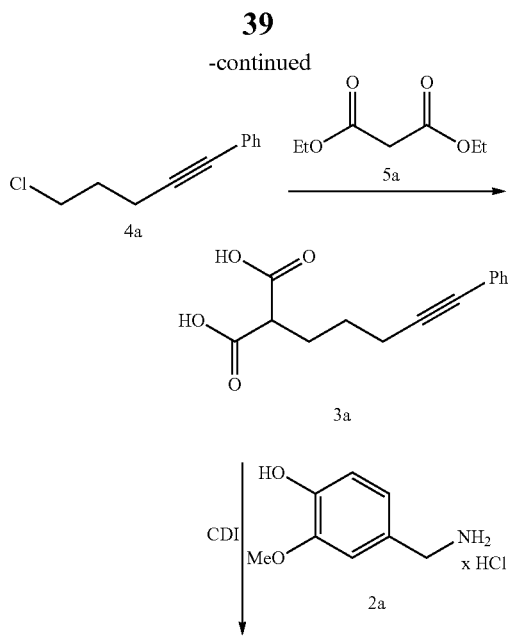

14. The method according to claim 12, further comprising a step of crystallising the phenylcapsaicin of formula (1a) by addition of 0.25-1 volume of water per volume of MTBE as a solvent to a 0.05-1 g/mL solution of the compound of formula (1a) in the MTBE and stirring at a temperature in the range from −5° C. to 5° C. for 2-24 hours.

15. The method according to claim 8, wherein the perfluoroalkylsulfonate is a triflate.

16. The method according to claim 8, wherein the sulfonate is a tosylate or a mesylate.

* * * * *